US011612384B2

(12) United States Patent
Duindam et al.

(10) Patent No.: US 11,612,384 B2
(45) Date of Patent: Mar. 28, 2023

(54) GRAPHICAL USER INTERFACE FOR DISPLAYING GUIDANCE INFORMATION IN A PLURALITY OF MODES DURING AN IMAGE-GUIDED PROCEDURE

(71) Applicant: INTUITIVE SURGICAL OPERATIONS, INC., Sunnyvale, CA (US)

(72) Inventors: Vincent Duindam, San Francisco, CA (US); Federico Barbagli, San Francisco, CA (US); Cristian Bianchi, Mountain View, CA (US); Christopher R. Carlson, Belmont, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 741 days.

(21) Appl. No.: 16/307,995

(22) PCT Filed: Jun. 29, 2017

(86) PCT No.: PCT/US2017/040067
§ 371 (c)(1),
(2) Date: Dec. 7, 2018

(87) PCT Pub. No.: WO2018/005842
PCT Pub. Date: Jan. 4, 2018

(65) Prior Publication Data
US 2020/0078103 A1   Mar. 12, 2020

Related U.S. Application Data

(60) Provisional application No. 62/486,879, filed on Apr. 18, 2017, provisional application No. 62/357,258, filed on Jun. 30, 2016.

(51) Int. Cl.
| | |
|---|---|
| *A61B 10/04* | (2006.01) |
| *A61B 34/00* | (2016.01) |
| *A61B 90/00* | (2016.01) |
| *A61B 1/00* | (2006.01) |
| *A61B 34/35* | (2016.01) |

(Continued)

(52) U.S. Cl.
CPC ........ *A61B 10/04* (2013.01); *A61B 1/000094* (2022.02); *A61B 34/25* (2016.02);
(Continued)

(58) Field of Classification Search
CPC ......... A61B 34/25; A61B 90/37; A61B 10/04; A61B 2090/378; A61B 34/35;
(Continued)

(56) References Cited

U.S. PATENT DOCUMENTS

| | | | | |
|---|---|---|---|---|
| 5,638,819 A * | 6/1997 | Manwaring | ............... | A61B 5/06 600/117 |
| 6,346,940 B1 * | 2/2002 | Fukunaga | ............... | G06T 15/20 382/103 |

(Continued)

FOREIGN PATENT DOCUMENTS

| | | |
|---|---|---|
| CN | 101854853 A | 10/2010 |
| CN | 105193503 A | 12/2015 |

(Continued)

OTHER PUBLICATIONS

Partial Supplementary European Search Report for Application No. EP18787852.5 dated Dec. 2, 2020, 17 pages.

(Continued)

*Primary Examiner* — Rene T Towa
(74) *Attorney, Agent, or Firm* — Haynes and Boone, LLP

(57) ABSTRACT

A method for displaying guidance information using a graphical user interface during an medical procedure comprises displaying, in a first mode of the graphical user interface, first image data from a perspective corresponding (Continued)

to a distal end of an elongate device. The first image data includes a virtual roadmap. The method also comprises transitioning from the first mode of the graphical user interface to a second mode of the graphical user interface. The transition is based on an occurrence of a triggering condition. The method also comprises displaying, in the second mode of the graphical user interface, second image data from a perspective corresponding to the distal end of the elongate device. The second image data includes a target indicator corresponding to a target location and an alignment indicator corresponding to an expected location of the medical procedure at the target location.

22 Claims, 14 Drawing Sheets

(51) Int. Cl.
| | |
|---|---|
| A61B 34/20 | (2016.01) |
| A61B 34/30 | (2016.01) |
| A61B 1/267 | (2006.01) |
| A61B 5/06 | (2006.01) |
| A61M 25/01 | (2006.01) |

(52) U.S. Cl.
CPC ............ *A61B 90/37* (2016.02); *A61B 1/0005* (2013.01); *A61B 1/2676* (2013.01); *A61B 5/066* (2013.01); *A61B 34/35* (2016.02); *A61B 2010/045* (2013.01); *A61B 2034/2051* (2016.02); *A61B 2034/2061* (2016.02); *A61B 2034/2065* (2016.02); *A61B 2034/301* (2016.02); *A61B 2090/374* (2016.02); *A61B 2090/378* (2016.02); *A61B 2090/3735* (2016.02); *A61B 2090/3762* (2016.02); *A61M 2025/0166* (2013.01)

(58) Field of Classification Search
CPC .... A61B 2034/2051; A61B 2034/2061; A61B 2034/301; A61B 1/0005; A61B 1/2676; A61B 5/066; A61B 2010/045; A61B 2034/2065; A61B 2090/3735; A61B 2090/374; A61B 2090/3762; A61B 2034/254; A61B 2034/102; A61B 2034/105; A61B 2034/107; A61B 90/30; A61B 2217/005; A61B 2217/007; A61B 2034/2059; A61B 34/20; A61B 1/00193; A61B 1/05; A61B 1/00009; A61B 1/0016; A61M 2025/0166
See application file for complete search history.

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 6,432,041 B1 | 8/2002 | Taniguchi et al. | |
| 6,671,538 B1 | 12/2003 | Ehnholm et al. | |
| 7,316,681 B2 | 1/2008 | Madhani et al. | |
| 7,772,541 B2 | 8/2010 | Froggatt et al. | |
| 7,930,065 B2 | 4/2011 | Larkin et al. | |
| 8,218,846 B2 | 7/2012 | Trumer et al. | |
| 8,412,307 B2 | 4/2013 | Willis et al. | |
| 8,672,836 B2 | 3/2014 | Higgins et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 9,603,668 B2 | 3/2017 | Weingarten et al. | |
| 2004/0082849 A1 | 4/2004 | Schweikard et al. | |
| 2004/0165810 A1 | 8/2004 | Fujita | |
| 2005/0182295 A1* | 8/2005 | Soper ................ | A61B 1/00172 600/117 |
| 2005/0261550 A1* | 11/2005 | Akimoto ............ | A61B 1/00009 600/101 |
| 2006/0013523 A1 | 1/2006 | Childers et al. | |
| 2007/0065077 A1 | 3/2007 | Childers et al. | |
| 2007/0270650 A1 | 11/2007 | Eno et al. | |
| 2007/0293721 A1 | 12/2007 | Gilboa | |
| 2008/0275467 A1 | 11/2008 | Liao et al. | |
| 2009/0156895 A1 | 6/2009 | Higgins et al. | |
| 2009/0198104 A1* | 8/2009 | Sugiyama .............. | A61B 1/018 600/146 |
| 2009/0227861 A1* | 9/2009 | Ganatra ................. | A61B 34/20 600/424 |
| 2010/0076305 A1 | 3/2010 | Maier-Hein et al. | |
| 2010/0141675 A1 | 6/2010 | Matsumoto | |
| 2010/0179418 A1 | 7/2010 | Mueller et al. | |
| 2010/0217117 A1* | 8/2010 | Glossop ............... | A61B 8/4245 600/424 |
| 2010/0249506 A1 | 9/2010 | Prisco et al. | |
| 2010/0317965 A1 | 12/2010 | Itkowitz et al. | |
| 2011/0319815 A1 | 12/2011 | Roelle et al. | |
| 2012/0065481 A1 | 3/2012 | Hunter et al. | |
| 2012/0089022 A1 | 4/2012 | House et al. | |
| 2012/0289843 A1* | 11/2012 | Chopra ................ | A61B 1/0051 600/508 |
| 2013/0179820 A1 | 7/2013 | Asami et al. | |
| 2013/0204124 A1 | 8/2013 | Duindam et al. | |
| 2013/0281838 A1* | 10/2013 | Trumer .................. | A61B 6/032 600/424 |
| 2014/0142422 A1 | 5/2014 | Manzke et al. | |
| 2014/0211213 A1 | 7/2014 | Weiss | |
| 2014/0350391 A1 | 11/2014 | Prisco et al. | |
| 2015/0073265 A1 | 3/2015 | Popovic et al. | |
| 2016/0000302 A1* | 1/2016 | Brown .................. | A61B 6/465 600/103 |
| 2016/0000517 A1 | 1/2016 | Kehat et al. | |
| 2016/0070878 A1 | 3/2016 | Soper et al. | |
| 2016/0073928 A1 | 3/2016 | Soper et al. | |
| 2016/0183841 A1 | 6/2016 | Duindam et al. | |
| 2016/0371883 A1* | 12/2016 | Merkine ................ | G06T 19/20 |
| 2017/0084027 A1 | 3/2017 | Mintz et al. | |
| 2017/0151027 A1 | 6/2017 | Walker et al. | |
| 2020/0030044 A1 | 1/2020 | Wang et al. | |
| 2020/0054399 A1 | 2/2020 | Duindam et al. | |
| 2020/0129239 A1 | 4/2020 | Bianchi et al. | |

FOREIGN PATENT DOCUMENTS

| | | |
|---|---|---|
| CN | 105636541 A | 6/2016 |
| CN | 106232001 A | 12/2016 |
| EP | 1103229 A2 | 5/2001 |
| EP | 3478161 A1 | 5/2019 |
| JP | H08332191 A | 12/1996 |
| JP | 2004513684 A | 5/2004 |
| JP | 2015519987 A | 7/2015 |
| JP | 2016030125 A | 3/2016 |
| WO | WO-9729709 A1 | 8/1997 |
| WO | WO-2007047782 A2 | 4/2007 |
| WO | WO-2008125910 A2 | 10/2008 |
| WO | WO-2009138871 A2 | 11/2009 |
| WO | WO-2011043982 A1 | 4/2011 |
| WO | WO-2014028394 A1 | 2/2014 |
| WO | WO-2015023665 A1 | 2/2015 |
| WO | WO-2015164587 A2 | 10/2015 |
| WO | WO-2016018646 A1 | 2/2016 |
| WO | WO-2016018648 A1 | 2/2016 |
| WO | WO-2016032846 A1 | 3/2016 |
| WO | WO-2016040080 A1 | 3/2016 |
| WO | WO-2018005680 A1 | 1/2018 |
| WO | WO-2018005842 A1 | 1/2018 |

OTHER PUBLICATIONS

Keller S.G., et al., "Equivalent Stress and Strain Distribution in Helical Compression Springs Subjected to Bending," The Journal of Strain Analysis for Engineering Design, Aug. 2011, vol. 46 (6), pp. 405-415.

(56) References Cited

OTHER PUBLICATIONS

Office Action dated Apr. 8, 2021 for Chinese Application No. 201780039120 filed Jun. 29, 2017, 28 pages.
Extended European Search Report for Application No. EP17821278 dated Jan. 23, 2020, 12 pages.
Extended European Search Report for Application No. EP17821289 dated Feb. 7, 2020, 9 pages.
International Preliminary Report on Patentability for Application No. PCT/US2017/040095, dated Jan. 10, 2019, 8 pages.
International Preliminary Report on Patentability for Application No. PCT/US2018/028190, dated Oct. 31, 2019, 11 pages.
International Search Report and Written Opinion for Application No. PCT/US2018/028190, dated Aug. 3, 2018, 14 pages.
International Preliminary Reporton Patentability for Application No. PCT/US2014/050715, dated Feb. 25, 2016, 14 pages.
International Search Report and Written Opinion for Application No. PCT/US2014/050715, dated Nov. 13, 2014, 17 pages.
International Search Report and Written Opinion for Application No. PCT/US2017/040095, dated Nov. 10, 2017, 11 pages.
Extended European Search Report for Application No. EP14836490.4, dated Mar. 24, 2017, 9 pages.
International Search Report and Written Opinion for Application No. PCT/US2017/040067, dated Aug. 30, 2017, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18787852.5 dated Mar. 5, 2021, 14 pages.
Office Action for Chinese Application No. CN20188030958, dated Aug. 24, 2022, 21 pages.

* cited by examiner

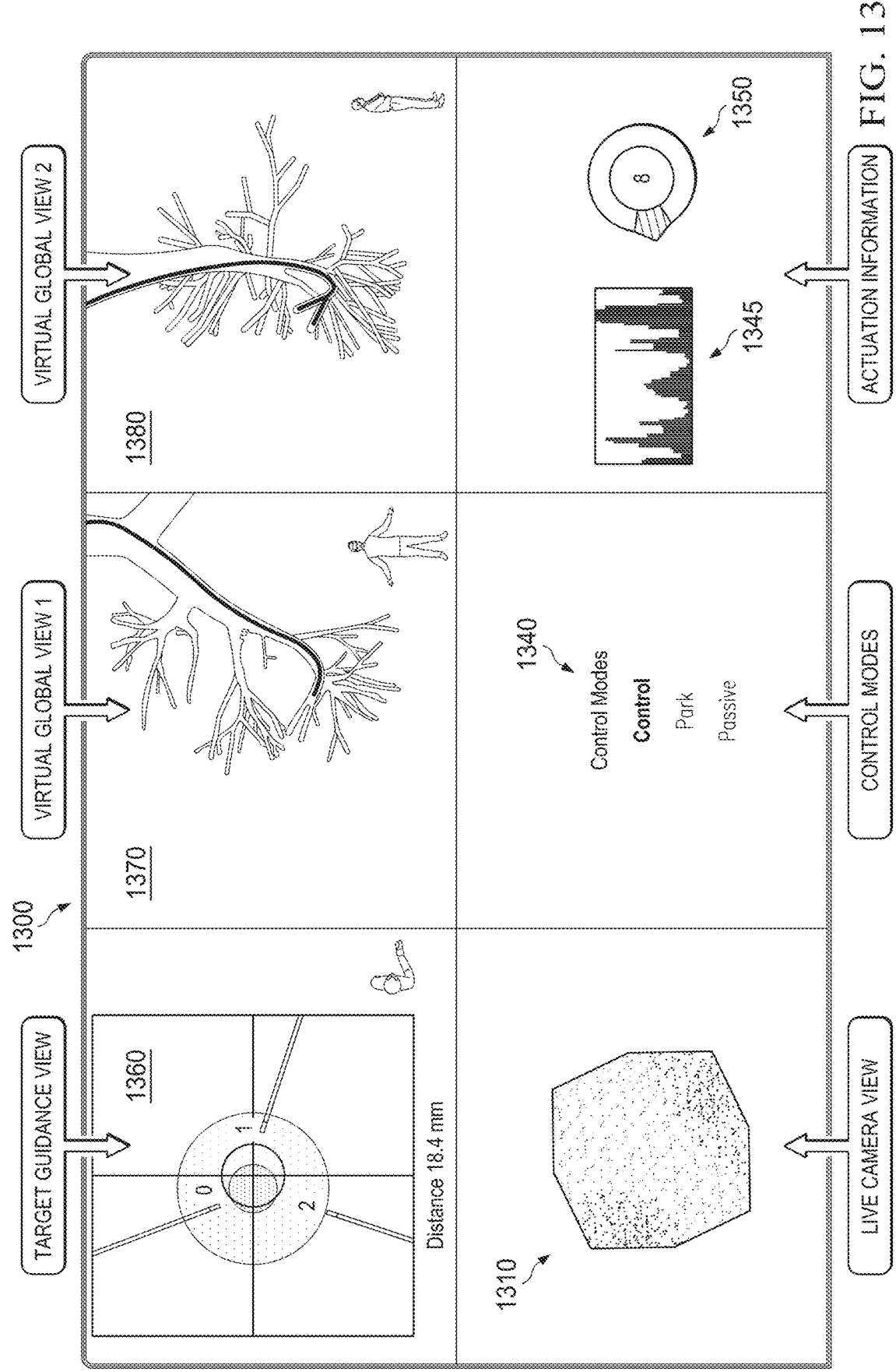

GRAPHICAL USER INTERFACE FOR DISPLAYING GUIDANCE INFORMATION IN A PLURALITY OF MODES DURING AN IMAGE-GUIDED PROCEDURE

RELATED APPLICATIONS

This patent application is the U.S. national phase of International Application No. PCT/US2017/040067, filed Jun. 29, 2017, which designated the U.S. and claims priority to and the benefit of the filing date of U.S. Provisional Patent Application 62/357,258, entitled "Graphical User Interface for Displaying Guidance Information in a Plurality of Modes during an Image-Guided Procedure," filed Jun. 30, 2016 and U.S. Provisional Patent Application 62/486,879, entitled "Graphical User Interface for Monitoring an Image-Guided Procedure," filed Apr. 18, 2017, all of which are incorporated by reference in their entirety. This application is also related to U.S. Provisional Patent Application 62/327,127, entitle "Graphical User Interface for Displaying Guidance Information During an Image-Guided Procedure," filed Jun. 30, 2016 which is hereby incorporated by reference in their entirety.

TECHNICAL FIELD

The present disclosure is directed to systems and methods for conducting an image-guided procedure and more particularly to systems and methods for displaying guidance information in a plurality of modes during an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Accordingly, it would be advantageous to provide a graphical user interface that supports intuitive control and management of flexible and/or steerable elongate devices, such as steerable catheters, that are suitable for use during minimally invasive medical techniques.

SUMMARY

The embodiments of the invention are best summarized by the claims that follow the description.

In some embodiments, a method for displaying guidance information using a graphical user interface during an medical procedure comprises displaying, in a first mode of the graphical user interface, first image data from a perspective corresponding to a distal end of an elongate device. The first image data includes a virtual roadmap. The method also comprises transitioning from the first mode of the graphical user interface to a second mode of the graphical user interface. The transition is based on an occurrence of a triggering condition. The method also comprises displaying, in the second mode of the graphical user interface, second image data from a perspective corresponding to the distal end of the elongate device. The second image data includes a target indicator corresponding to a target location and an alignment indicator corresponding to an expected location of the medical procedure at the target location.

In some embodiments, a system for displaying guidance information, using a graphical user interface, comprises an elongate device including a flexible body. The system also includes one or more processors configured to display, in a first mode of the graphical user interface, first image data from a perspective corresponding to a distal end of the elongate device. The first image data includes a virtual roadmap. The one or more processors is also configured to transition from the first mode of the graphical user interface to a second mode of the graphical user interface. The transition is based on an occurrence of a triggering condition. The one or more processors is also configured to display, in the second mode of the graphical user interface, second image data from a perspective corresponding to the distal end of the elongate device. The second image data includes a target indicator corresponding to a target location and an alignment indicator corresponding to an expected location of the medical procedure at the target location.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 13 is a screenshot of a multi-modal graphical user interface in an alignment mode according to some embodiments.

Figure 1:
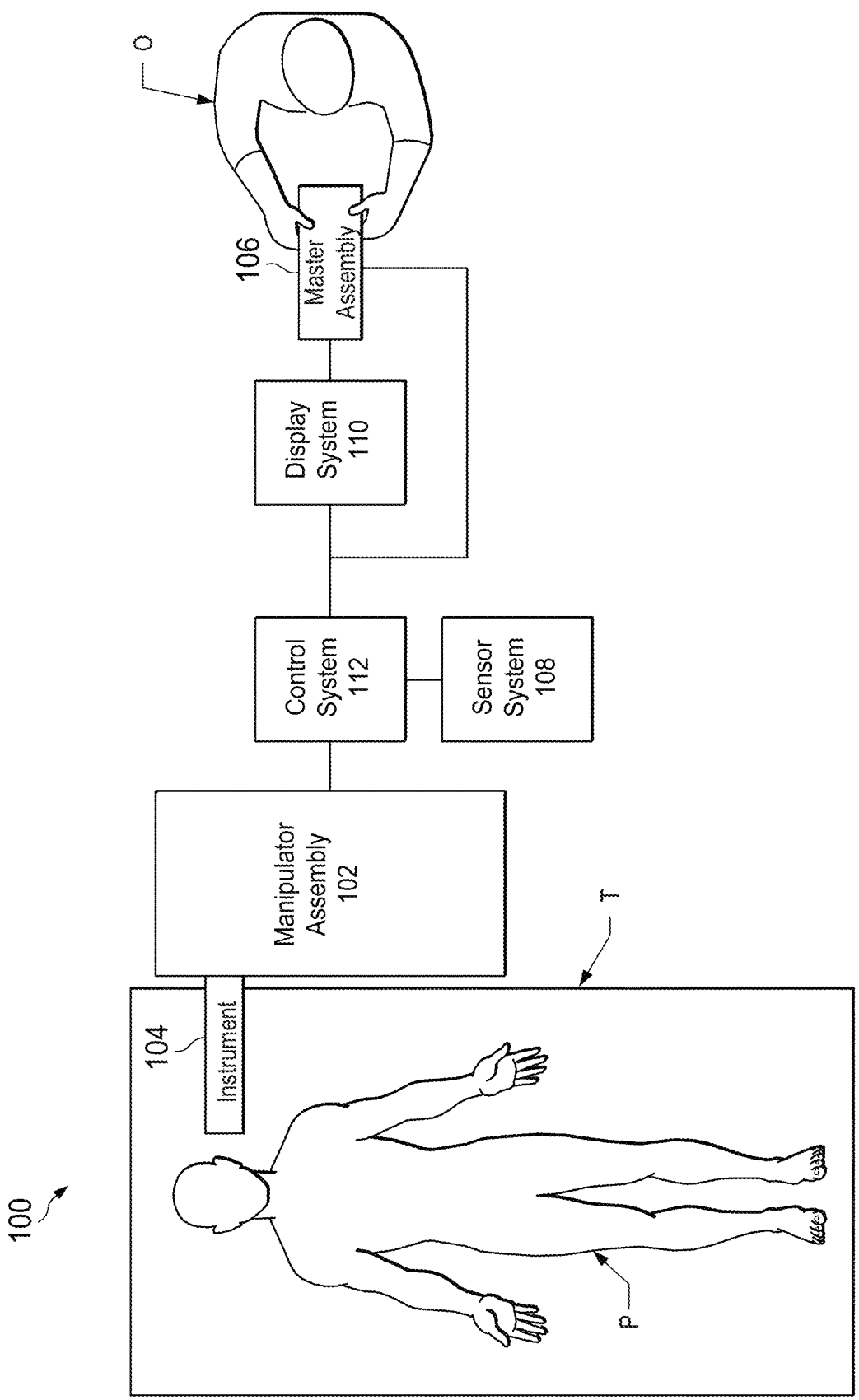
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a physician's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104;

and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
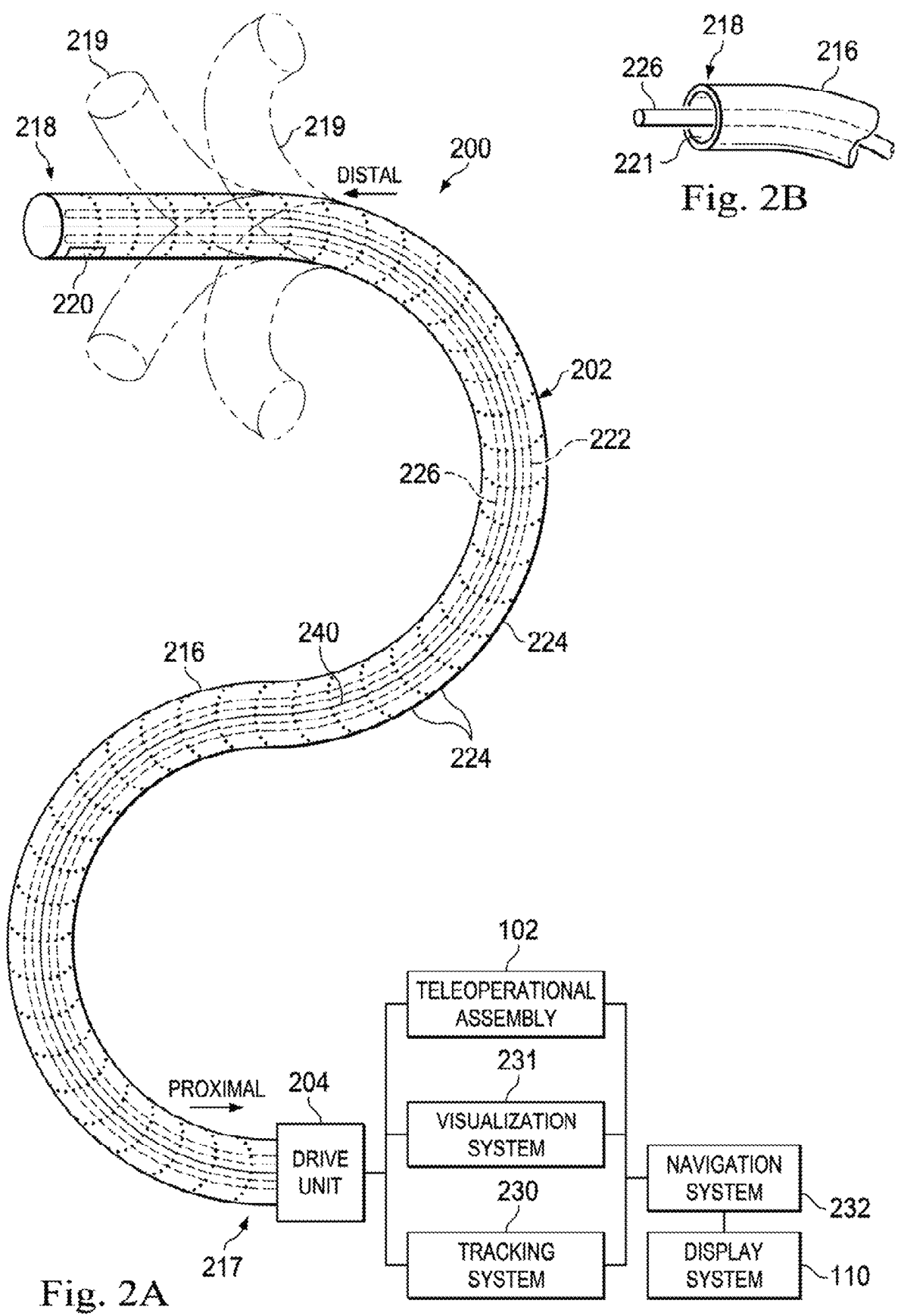
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having proximal end 217 and distal end 218 (also called "tip portion 218"). In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of flexible body 216 at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 216 may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may comprise, or be a component of, an EM sensor system including one or more conductive coils that may be subjected to an externally generated electromagnetic field. Each coil of such an EM sensor system implementing position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician, clinician, or surgeon or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
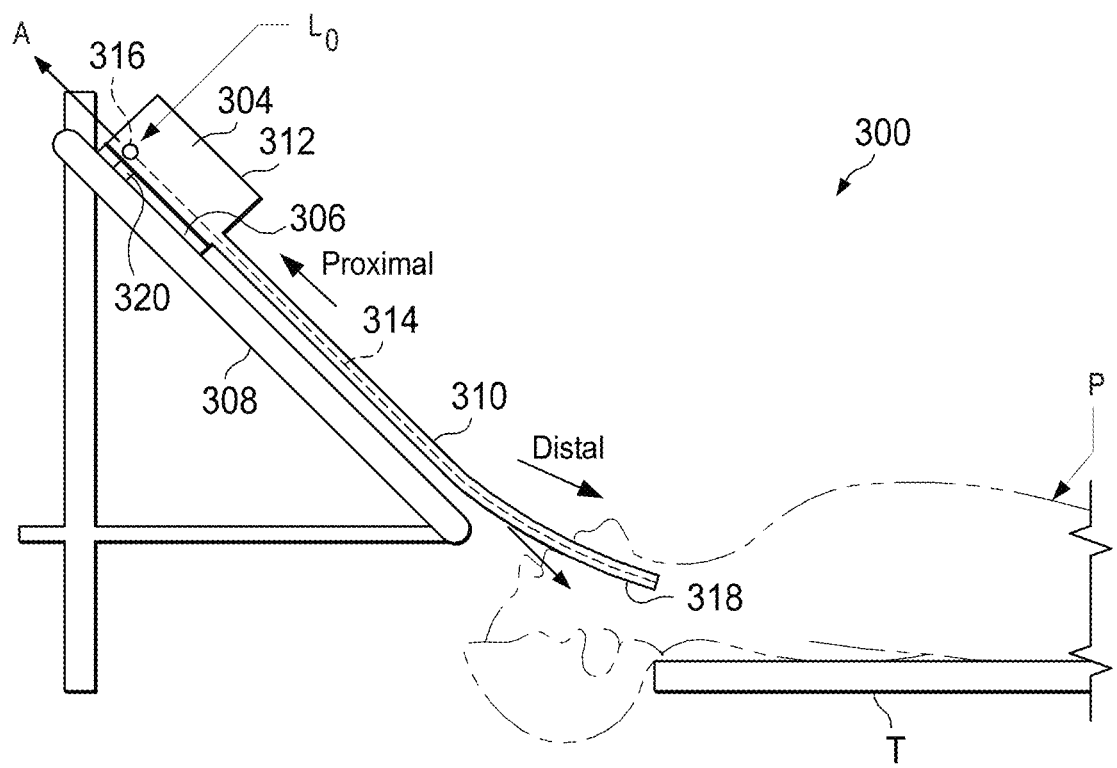
FIGS. 3A and 3B are simplified diagrams of side views of a patient coordinate space including a medical instrument mounted on an insertion assembly according to some embodiments.
Figure 3B:
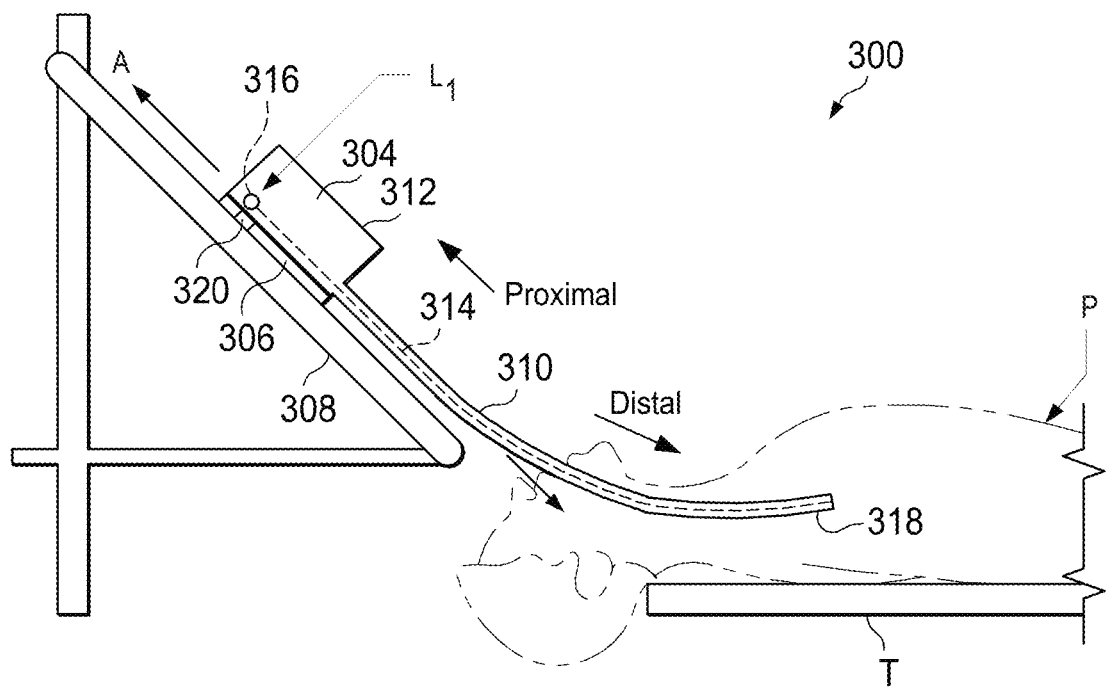

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position LX may further be used as an indicator of the distance or insertion depth to which distal end 318 of elongate device 310 is inserted into the passageways of the anatomy of patient P.

Figure 4A:
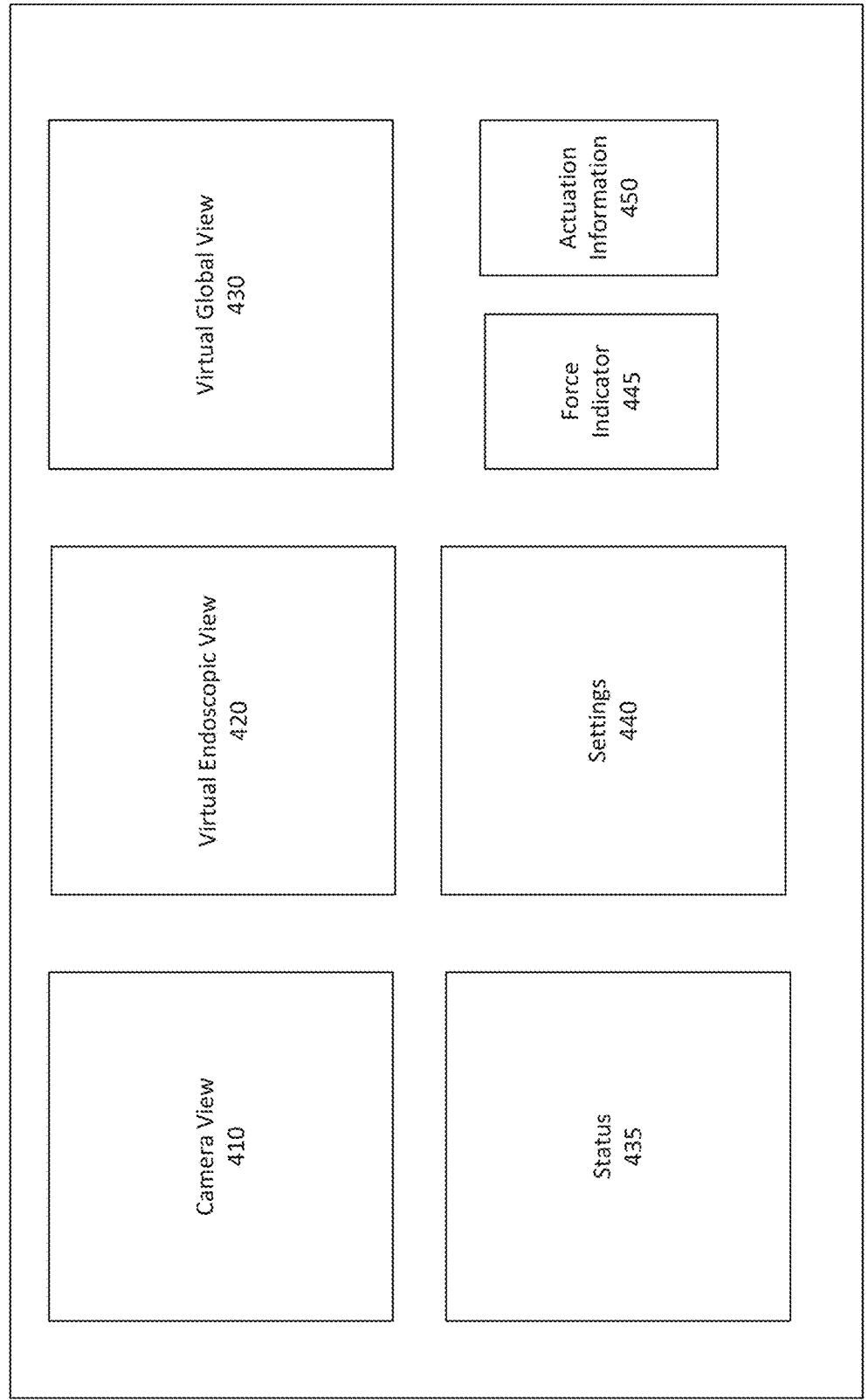
FIG. 4A is a simplified diagram of a multi-modal graphical user interface in a traversal mode according to some embodiments.
Figure 4B:
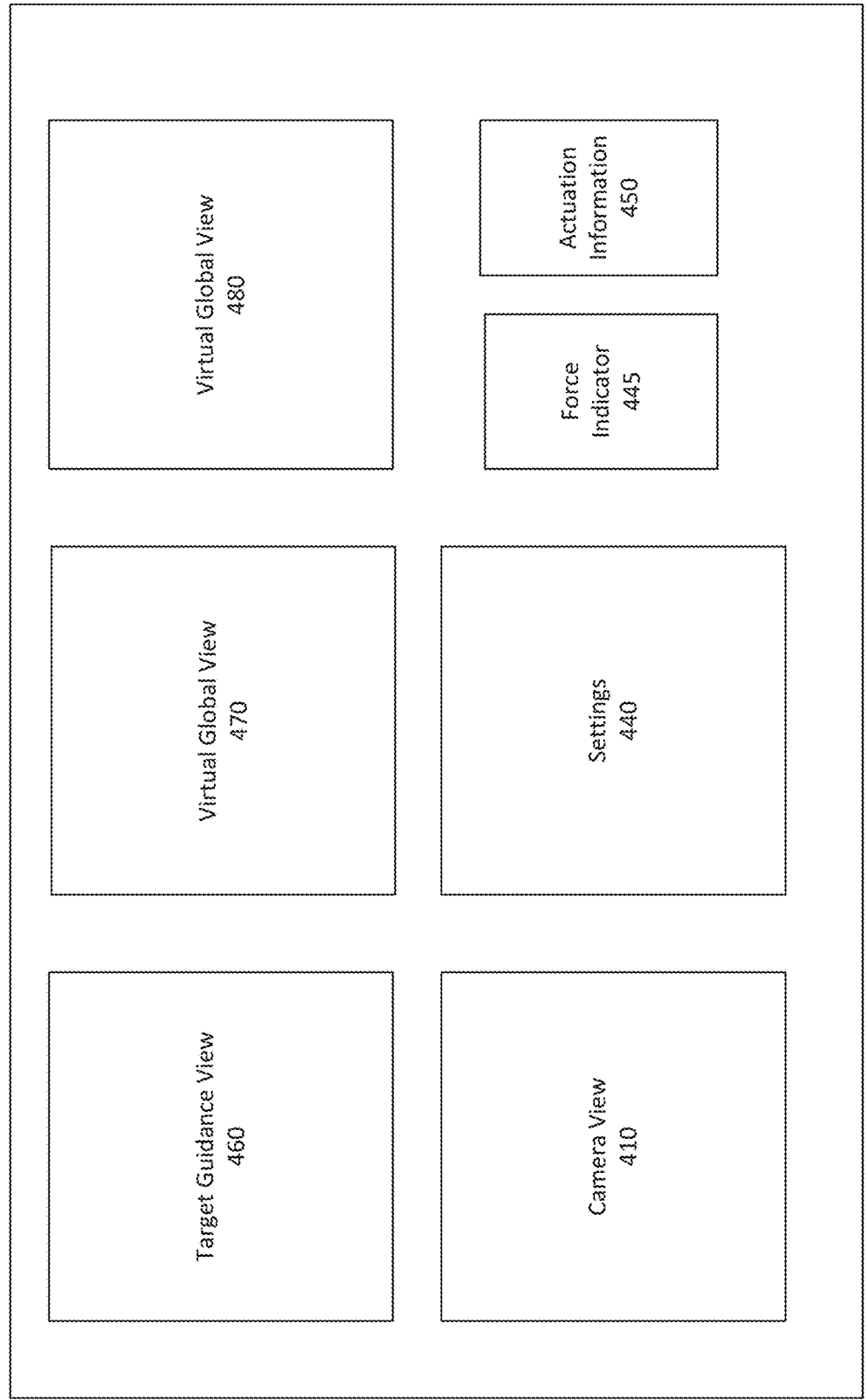
FIG. 4B is a simplified diagram of a multi-modal graphical user interface in an alignment mode according to some embodiments.

FIGS. 4A and 4B are simplified diagrams of a multi-modal graphical user interface 400 displayable on display system 110 according to some embodiments. In some embodiments consistent with FIGS. 1-3, multi-modal graphical user interface 400 may be used to assist an operator, such as a physician, clinician or surgeon O, during the operation and/or control of a medical instrument system, such as teleoperated medical system 100 and/or medical instrument system 200. For example, the medical instrument system may include an elongate device, such as elongate device 202, and one or more medical instruments, such as medical instruments 226, inserted into a flexible body of the elongate device.

Multi-modal graphical user interface 400 displays information in one or more windows 410-480 that are viewable to the operator. Although five or six concurrently viewable windows on a single screen are depicted in FIGS. 4A and 4B, respectively, it is to be understood that graphical user interface 400 may display any suitable number of windows on any suitable number of screens. In some examples, the number of concurrently viewable windows may be varied by opening and closing windows, minimizing and maximizing windows, moving windows between a foreground and background of multi-modal graphical user interface 400, switching between screens, and/or otherwise fully or partially obscuring windows from view. Similarly, the arrangement of windows 410-480—including their size, shape, orientation, ordering (in case of overlapping windows), and/or the like—may vary and/or may be user-configurable.

According to some embodiments, windows 410-480 may display image data, sensor data, indicators, control modes, and/or any combination thereof. In some examples, image data may include pre-operative or intra-operative image data. Image data may be presented as two-dimensional, three-dimensional, or four-dimensional (including e.g., time based or velocity based information) live images and/or as images of calculated models created from pre-operative or intra-operative image data sets. In some examples, images of calculated models may be derived from sensor data, and may include models of instruments introduced into the anatomy. In some examples, the calculated models may be created from empirical data (in addition to or instead of image data) and/or may be based on a predetermined geometry of instruments and/or human anatomy. In some examples, indicators may include graphical and/or alphanumeric indicators. In some examples, controls may include buttons, text inputs, navigation panels, taskbars, icons, alerts, and/or the like. According to some embodiments, multi-modal graphical user interface 400 may include a settings window 440 that displays available control modes, current control mode, and/or a list of settings associated with the medical instrument.

FIGS. 4A and 4B depict multi-modal graphical user interface 400 in a traversal mode and an alignment mode, respectively. According to some embodiments, the traversal mode may be suitable for display when the elongate device is being navigated through the patient's body over substantial distances, e.g., being navigated through anatomical passageways towards a target location using adjustment of the pose in combination with substantial changes in insertion. According to some embodiments, the target location may correspond to the target surgical location and/or target anatomical location, as discussed above with respect to FIGS. 2A and 2B. The alignment mode may be suitable for display during adjustment of the pose and/or small changes in insertion of the elongate device, such as when collecting a biopsy sample and/or performing laser ablation at the target location.

In some examples, the traversal mode is used when a distal end of the elongate device is far from a target location and substantial movement (e.g., insertion, retraction, articulation, and/or the like) of the elongate device is expected. For example, the traversal mode may be used for exploring anatomical passageways and/or when tracing a predetermined route leading to a target location. Conversely, the alignment mode is used when the distal end of the elongate device is near the target location and fine adjustments to the pose of the elongate device are expected (e.g., when manually and/or automatically orienting the distal end of the elongate device at an optimal angle and/or distance from the target location for successful delivery of a needle). For example, the alignment may be used when the elongate device is within two or three centimeters of the target location, and/or when there is a line of sight between the elongate device and the target location (i.e., there are no obstructions and/or bends in anatomical passageways that separate the target location from the elongate device). In some examples, the alignment mode may be used when no live camera feed from the distal end of the elongate device is available (i.e., when driving "blind"), such as after an endoscope used to aide in navigation during traversal mode is removed from the elongate device in preparation for the surgical procedure at the target location.

In some examples, multi-modal graphical user interface 400 may transition between the traversal and alignment modes manually and/or automatically. A user initiated transition may be performed by the operator by, for example, clicking a button, manually flipping a switch, pressing a pedal using a touchpad, announcing an audible command, and/or any other suitable switching input from the user. In some examples, an automatic transition may be performed based on the occurrence of one or more triggering events during the course of a medical procedure. For example, a triggering condition may include removing a camera probe from the elongate device, the camera probe providing image data that is displayed via multi-modal graphical user interface 400 in the traversal mode. In some examples, the removal of the camera probe from the elongate device may be detected based on a change in shape of the elongate device, as determined using a tracking system, such as tracking system 230 that includes a shape sensor. In some examples, the removal of the camera probe from the elongate device may be detected based on a change in the image data provided by the camera probe, as determined using an image processor. In some examples, the change in image data may be provided from a real imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The change in image data can include a new image being acquired using the imaging technology at a different angle relative to a target or at a different time in the procedure. The triggering condition may include the attachment or disconnection of the imaging technology from the system. In some examples, a triggering condition may include inserting a medical instrument into the elongate device. Like the removal of the camera probe from the elongate device, the insertion of the medical instrument into the elongate device may be determined based on a change in shape of the elongate device. In some examples, the triggering condition may include detecting that the distal end of the elongate device is within a predetermined distance of the target location, such as two or three centimeters. In some examples, the triggering condition may include determining that there is a line of sight between the distal end of the elongate device and the target location (i.e., no obstructions and/or bends in anatomical passageways). In some examples, the triggering condition may include detecting that there are no remaining branches in the anatomical passageways separating the distal end of the elongate device and the target location, meaning that there is no remaining risk of getting "lost" by navigating down the wrong branch. In some examples, the triggering condition may include reaching the end of a predetermined route to the target location. In some examples, the triggering condition may include detecting that the operator has stopped inserting the elongate device (i.e., when the elongate device has been "parked"). In some examples, the operator may have the option of overriding the automatic mode selection by manually changing the automatic mode selection.

In some examples, any suitable combination of one or more triggering conditions may be used to automatically switch between the traversal and alignment modes. For example, a triggering condition may include detecting that both of the following conditions are concurrently satisfied: (1) the elongate device is within a predetermined distance of the target location and (2) the operator has stopped inserting the elongate device.

In the traversal mode, as depicted in FIG. 4A, multi-modal graphical user interface 400 may display a camera view window 410, a virtual endoscopic view window 420, a virtual front view window 430, a status window 435, a settings window 440, a force indicator window 445, and an actuation information window 450. Camera view window 410 displays camera data captured by a visualization system, such as a visualization system of medical instrument 104. For example, the camera data may include a live video feed captured by an endoscope and/or a stereoscopic or monoscopic camera at or near a distal end of the elongate device. One or more indicators and/or controls may be superimposed on and/or displayed alongside the image data to assist the operator in controlling the elongate device.

Virtual endoscopic view window 420 displays virtual image data from a viewpoint corresponding to a distal end of the elongate device. In this regard, virtual endoscope view window 420 simulates the field of view of an endoscope. According to some embodiments, the virtual image data may be generated by a virtual visualization system, such as virtual visualization system of control system 112 using, for example a preoperative image dataset. According to some embodiments, the virtual image data displayed by virtual endoscope view window 420 may be augmented to display supplemental guidance information to the operator. An embodiment of virtual endoscope view window 420 is discussed in greater detail below with reference to FIG. 5.

Virtual global view window 430 displays virtual image data from a viewpoint corresponding to a zoomed out view of patient P. In this manner, virtual global view window 430 simulates the field of view of an observer, such as a physician O. In some examples, the view orientation can be selected manually and/or automatically. Like virtual endoscope view window 420, the virtual image data may be generated by a virtual visualization system, such as virtual visualization system of control system 112. In some examples, the virtual image data may display the real time position of the elongate device in the patient anatomy. An embodiment of virtual global view window 430 is discussed in greater detail below with reference to FIG. 6.

When windows 410-430 are displayed concurrently, the images displayed in windows 410-430 advantageously allow the operator to concurrently monitor and/or visualize the vicinity of the distal end of the elongate device (via camera view window 410 and/or virtual endoscope view window 420) as well as the broader pose of the elongate device (via virtual global view window 430) in relation to patient anatomy.

Status window 435 displays system status during system setup and/or during system use. In some examples status can include presence of the probe, presence of a medical tool, engagement of a sterile adaptor or ISA, error or FRL status, correct placement of the elongate device, and incorrect placement of elongate device when elongate device has shifted positions. The status window can also provide instructions including when to install or remove the elongate device, how to recover from a system fault, or other workflow instructions. The information may be colored or be differently sized based on properties such as the relative urgency, type, or intended audience of the information.

Force indicator window 445 displays information regarding the force exerted by actuators or motors during advancement of the elongate device. The force indicator can provide information regarding the system state. In some examples, a high indicator of force for an extended period of time can be indicative of components of the system such as drapes, medical devices, etc. caught or stuck during insertion. In some examples, the force displayed may be the instantaneous force at that time. In other examples, the force displayed may be indicating some recent history of the force, for example a graph of the force over the last 30-120 seconds. An embodiment of force indicator window 455 is discussed in greater detail below with reference to FIG. 7.

An actuation information window 450 displays information regarding the actuation of a steerable portion of the elongate device. In some examples, the actuation information may be used to alert the operator to problems and/or potential problems that arise during the steering of the elongate device. The actuation information may additionally provide assistance to the operator in correcting, avoiding, and/or alleviating a detected problem. An embodiment of actuation information window 450 is discussed in greater detail below with reference to FIG. 8.

In the alignment mode, as depicted in FIG. 4B, multi-modal graphical user interface 400 may display a target guidance view window 460, virtual global view windows 470 and 480, camera view window 410, settings window 440, force indicator window 445, and actuation information window 450. Target guidance view window 460 displays a target location from a viewpoint corresponding to a distal end of the elongate device. In some examples, target guidance view window 460 may replace virtual endoscopic view window 420 when multi-modal graphical user interface 400 switches from the traversal mode to the alignment mode. According to some embodiments, target guidance view window 460 may display guidance information designed to assist the operator in steering the elongate device to the target location from close range. An embodiment of target guidance view window 460 is discussed in greater detail below with reference to FIG. 9.

Virtual global view windows 470 and 480 display virtual image data similar to virtual global view window 430. According to some embodiments, the perspective of virtual global view windows 470 and 480 may be rotated relative to virtual global view window 430 and/or each other. In some examples, the perspectives of virtual global view windows 470 and 480 may be selected manually and/or automatically. In some examples, the perspectives have a fixed offset (e.g., a 90 degree offset to preserve orthogonality), such that rotating one of the perspectives causes the other to automatically rotate by a corresponding amount. In some examples, one of the perspectives may be automatically selected such that a needle extending from the elongate device appears in-plane. In some examples, one of the perspectives may be automatically selected to match the view of a fluoroscopic imaging device used to observe the procedure. According to some embodiments, the virtual image data displayed in virtual global view windows 470 and 480 may be simplified relative to virtual global view window 430 in order to reduce the amount of processing used to generate the virtual image data. An embodiment of virtual global view windows 470 and 480 is discussed in greater detail below with reference to FIG. 10.

Camera view window 410 is optionally included in multi-modal graphical user interface 400 in the alignment mode. However, in some embodiments, the camera (e.g., an endoscope) may be disabled and/or withdrawn when multi-modal graphical user interface 400 is in the alignment mode. Accordingly, multi-modal graphical user interface 400 may not include a camera view window in the second mode. Alternately or additionally, camera view window 410 may display an indicator, such as text, to communicate to the operator that image data from a camera is unavailable.

In some examples, multi-modal graphical user interface 400 may provide one or more additional visual indicators when transitioning from traversal mode to alignment mode. In some examples, a screen border of graphical user interface 400 may transition from a first color, texture, shade, and/or transparency in the traversal mode to a second color, texture, shade, and/or transparency in the alignment mode. For example, the screen border may change from yellow in traversal mode to red in alignment mode. In some examples, multi-modal graphical user interface 400 may include an icon that changes colors in a similar manner.

Figure 5:
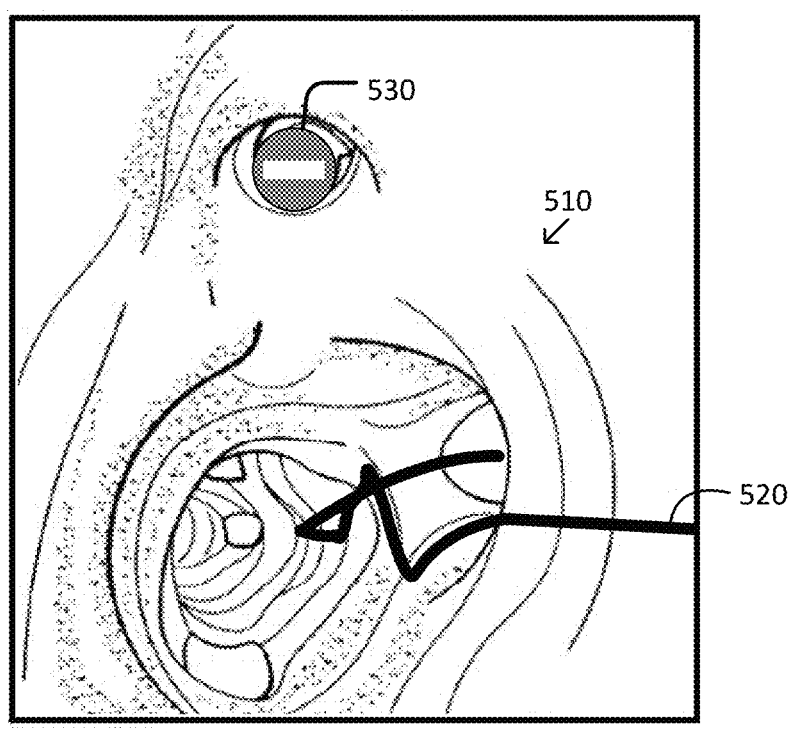
FIG. 5 is a simplified diagram of a window for displaying virtual endoscopic images according to some embodiments.

FIG. 5 illustrates an exemplary window 500 for displaying virtual endoscopic images according to some examples. According to some embodiments consistent with FIGS. 1-4, window 500 may correspond to virtual endoscopic view window 420. As depicted in FIG. 5, window 500 displays anatomical features 510 from a perspective of forward-looking out of a distal end of an elongate device inserted into a patient body. In some examples, anatomical features 510 may include anatomical features of interest, such as anatomical passageways, blood vessels, organs, and/or the like. Anatomical features 510 may be displayed using virtual renderings and/or images generated from a preoperatively or intra-operatively acquired image dataset. In some examples, anatomical features 510 may be displayed as translucent features and/or as outlines such that features inside of and/or behind a given anatomical feature may be concurrently displayed in window 500.

A virtual roadmap 520 displayed in window 500 indicates a predetermined route leading to a target location. Virtual roadmap 520 serves as a guide to the operator when steering the elongate device through the patient anatomy. For example, virtual roadmap 520 may indicate which branches in the anatomical passageways to steer the elongate device towards and/or away from. As depicted in FIG. 5, virtual roadmap 520 is displayed as a line winding through the anatomical passageways along the predetermined route. In some examples, the color, shade, texture, and/or transparency of the line may vary to indicate proximity to the target location, deviation from the predetermined route, presence of a bend, branch, and/or constriction in the anatomical passageway (which may be pre-computed to alert the operator of impending tricky maneuvers), diameter of the anatomical passageway, and/or other supplementary information. In some examples, a variety of alternate or additional mapping indicators may be included as part of virtual roadmap 520. For example, virtual roadmap 520 may include one or more arrows indicating a direction in which to steer. In some examples, virtual roadmap 520 may include one or more alphanumeric indicators that indicate a remaining distance to the target location, remaining time to reach the target location, identity of the anatomical passageway (e.g., trachea, RMB, B6, and/or the like), and/or the like. In some examples, virtual roadmap 520 may include tick marks, such as distance-to-target tick marks. In some examples, navigating the elongate device in an incorrect direction off of the predetermined route may cause one or more walls of the anatomical passageways to be rendered transparently so that virtual roadmap 520 can be seen through the obstruction. In some examples, virtual roadmap 520 may include audio instructions (e.g., "turn right") and/or haptic feedback (e.g., a vibration of the surgical controls when the elongate device deviates from the predetermined route).

A roadblock indicator 530 displayed in window 500 indicates an undesirable anatomic feature or an anatomical passageway and/or direction in which the elongate device should not or cannot be steered. As depicted in FIG. 5, roadblock indicator 530 includes an icon placed over to the anatomical passageway. In some examples, the icon may include a "do not enter" sign, stop sign, caution symbol, red or yellow light, and/or the like. In some examples, roadblock indicator 530 may be located on and/or adjacent to an anatomical passageway in which the elongate device has previously been steered. In furtherance of such embodiments, roadblock indicator 530 may display clinical information associated with previous tests and/or procedures performed in said anatomical passageway (e.g., "biopsy results negative"). In some examples, roadblock indicator 530 may be located on and/or adjacent to an anatomical passageway in which it would be dangerous and/or impossible to steer the elongate device. For example, roadblock indicator 530 may mark an anatomical passageway that is too narrow to fit the elongate device or a bend of the anatomical passageway may be too tight (e.g. the bend radius may be too tight for the elongate device to traverse). In some examples, roadblock indicator 530 may be displayed by varying the color, shade, texture, and/or transparency of the anatomical passageways to be avoided. In some examples, roadblock indicator 530 may include audio feedback (e.g., "warning" or "stop") and/or haptic feedback (e.g., a vibration of the surgical controls when the elongate device is steered toward the forbidden route). In some examples, roadblock indicator 530 may appear when the operator attempts to steer the elongate device in the incorrect direction and may subsequently disappear when the operator corrects the course of the elongate device (e.g., by retracting the elongate device and/or steering the elongate device back towards the desired path).

Figure 6:
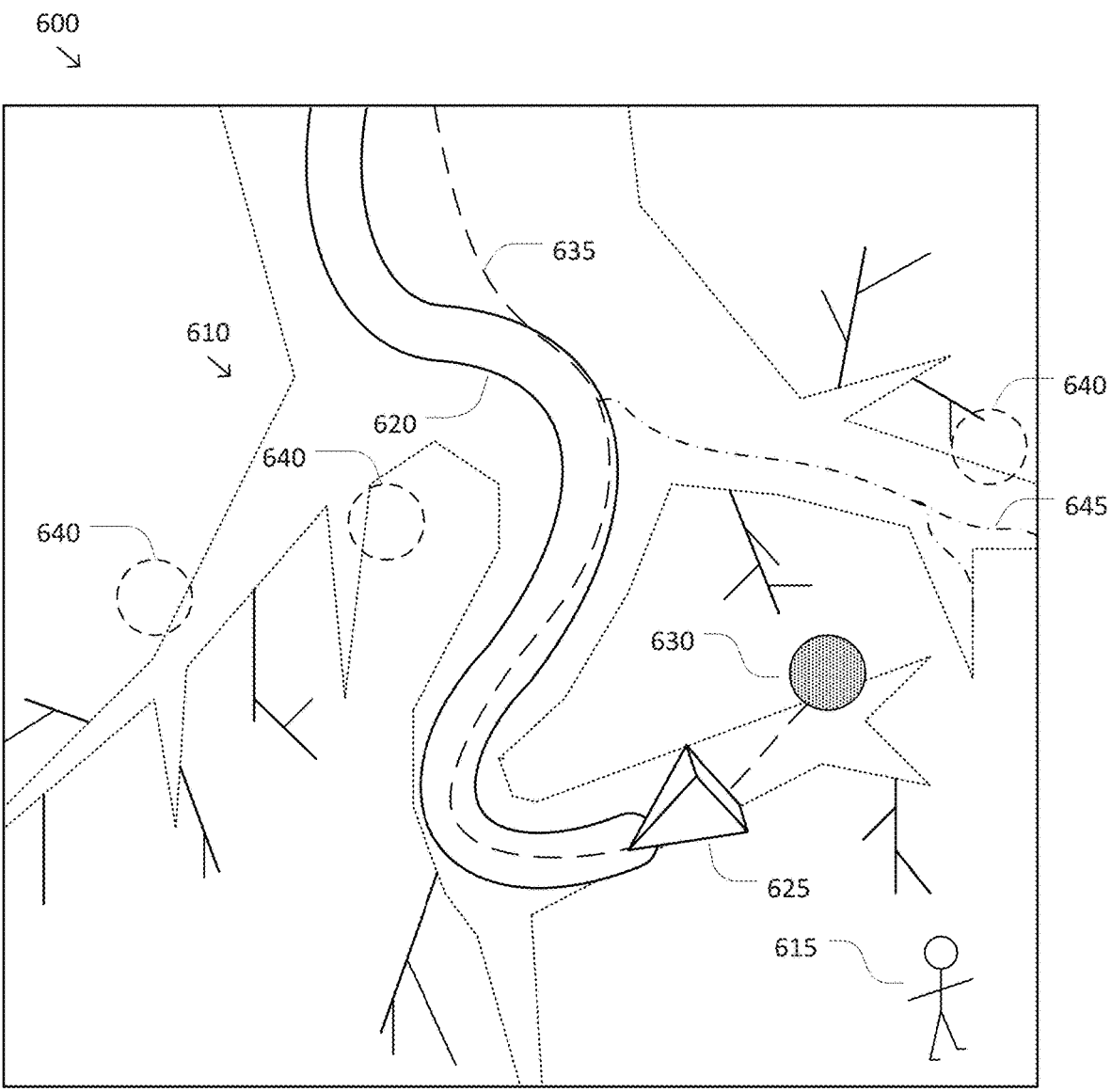
FIG. 6 is a simplified diagram of a window for displaying virtual global images in a traversal mode according to some embodiments.

FIG. 6 illustrates an exemplary window 600 for displaying virtual global images in a traversal mode according to some examples. According to some embodiments consistent with FIGS. 1-4, window 600 may correspond to virtual global view window 420. As depicted in FIG. 6, window 600 displays anatomical features 610 and an elongate device 620 from a "global" perspective (e.g., a perspective of physician O while standing over patient P). In some examples, anatomical features 610 may include anatomical features of interest, such as anatomical passageways, blood vessels, organs, and/or the like. Anatomical features 610 may be displayed using virtual renderings and/or images generated, for example from a preoperatively or intra-operatively acquired medical imaging dataset. In some examples, anatomical features 610 may be displayed as translucent features and/or as outlines such that features inside of and/or behind a given anatomical feature may be concurrently displayed in window 600.

In some examples, the perspective of window 600 is indicated using an orientation indicator 615. As depicted in FIG. 6, the orientation indicator 615 may include a virtual figurine positioned at an angle that represents the orientation of the global view relative to the patient body. According to some embodiments, the perspective of window 600 may change over time, in which case orientation indicator 650 may be continuously updated to reflect the changing viewing angle. In some examples, orientation indicator 615 may include an icon, such as an arrow, that indicates a reference axis or direction, such as the direction of gravity. In some embodiments, orientation indicator 615 may include alphanumeric indicators such as text labels (e.g., "front view" or "side view") and/or coordinate labels (e.g. polar coordinates representing the viewing angle). In some examples, orientation indicator 615 may utilize text labels based on x-ray labeling schemes (e.g., "AP" for anteroposterior view and "PA" for posteroanterior view). Orientation indicator 615 may be located in any suitable position within and/or near window 600. In some examples, orientation indicator 615 may be located outside of window 600 so as not to obscure the virtual images.

In some examples, a field of view indicator 625 is displayed at a distal end of elongate device 620. According to some embodiments consistent with FIG. 4a, field of view indicator 625 provides a representation of the field of view seen in camera view window 410 and/or virtual endoscopic view window 420. In this manner, the operator may intuitively grasp the correspondence between the images seen in each of the windows. In some examples, field of view indicator 625 may be displayed as a prism and/or conical shape. In some examples, a miniature version of camera view window 410 and/or virtual endoscopic view window 420 may be projected onto the flat face of field of view indicator 625 to further reinforce the correspondence between each of the various windows. In some examples, field of view indicator 625 may be represented as rays emanating from the distal end of elongate device 620.

A current target location 630 is displayed in window 600. Consistent with embodiments discussed above in FIGS. 1-4, current target location 630 may correspond to the target surgical location and/or target anatomical location. In some examples, current target location 630 may be depicted as a circle, sphere, target (e.g., concentric circles), crosshairs, and/or any other suitable shape/design. In some examples, the shape of current target location 630 may be determined using pre-operative voxel data, such as medical imaging data. For example, current target location 630 may depict realistically the shape of a tumor. In some examples, the color, texture, shading, and/or transparency of current target location 630 may be variable. In some examples, current target location 630 may blink and/or otherwise have a time-varying aspect to its appearance to draw the attention of the operator. A virtual roadmap 635 may display a predetermined route leading to current target location 630. In some examples, virtual roadmap 635 may have substantially similar attributes and/or functionality as virtual roadmap 520, as discussed previously with respect to FIG. 5.

In some examples, one or more previous and/or future target locations 640 may also be displayed in window 600. Target locations 640 generally serve an informational purpose to help orient the operator and provide context for the current stage of the procedure. In some examples, target locations 640 may be selectable, in which case the selected target location becomes the current target location. In some examples, the size, color, texture, shade, and/or transparency of target locations 640 may be different from the attributes of current target location 630 as to make them distinguishable. Similarly, historical path 645 may indicate a path and/or a portion of a path that elongate device 620 has previously traveled along during the procedure. For example, historical path 645 may represent a path taken during calibration, during navigation to a previous target location, and/or during a previous attempt to navigate to current target location 630. In some examples, various portions of historical path 645 may be displayed using different colors, textures, shades, and/or transparencies to indicate the purpose and/or time of the particular portion of the path (e.g., calibration, previous attempts to reach current target location 630, and/or previous attempts to reach different target locations). In some examples, historical path 645 may be temporarily displayed and subsequently hidden from view. For example, historical path 645 may be temporarily displayed to verify the registration of anatomical features 610 and historical path 645. That is, historical path 645 is expected to be aligned with anatomical features 610 when registration is correct and misaligned when registration is incorrect. When registration is incorrect, the operator may address the problem by, for example, retracting elongate device 620 and/or recalibrating as appropriate. When registration is correct, the operator may disable/hide historical path 645 and proceed with the navigation of elongate device 620 to target location 630.

Figure 7:
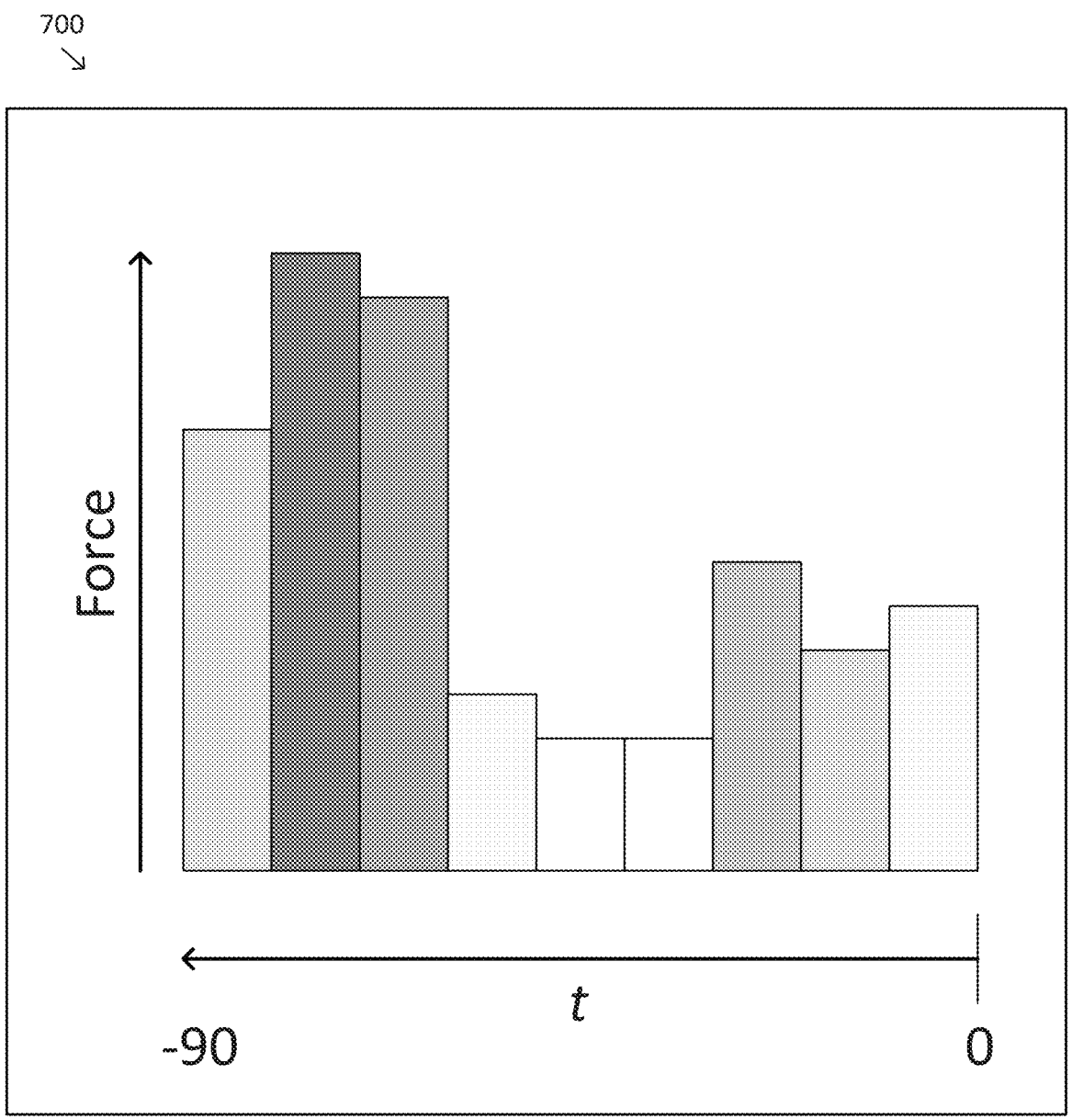
FIG. 7 is a simplified diagram of a window for displaying force indicator information according to some embodiments

FIG. 7 is a simplified diagram of a window 700 for displaying force indicator information according to some embodiments. According to some embodiments consistent with FIGS. 1-4, window 700 may correspond to force indicator window 445. In some examples, the information provides a representation of insertion force exerted by motors or actuators used to advance the elongate device. The information can be displayed in the form of a scrolling bar graph providing a history of insertion force as it changes over time with a left most vertical bar on the graph representing an oldest force measurement and a right most vertical bar on the graph representing a most recent force measurement. In some examples, the time difference between the oldest force measurement and the most recent force measurement could be 90 seconds, but could represent any greater or smaller period of time. The size of the vertical bar can be indicative of a magnitude of the force measurement. In some examples, the vertical bars can be shown in different colors, shades, textures, and/or transparencies representative of the magnitude of the force measurement. In some examples red can be used to indicate a force measurement above a preset threshold, yellow can be used to indicate a force measurement in a preset middle threshold range, and green can be used to indicate a force measurement below a preset threshold.

In certain embodiments, the force measurement can be obtained with various sensors and computed with various algorithms. For example the force from a force sensor at the distal end of the elongate device, or as measured by the insertion motor. The measured force may then be used to compute the force of interest, perhaps subtracting modeled gravitational forces or friction forces.

Figure 8:
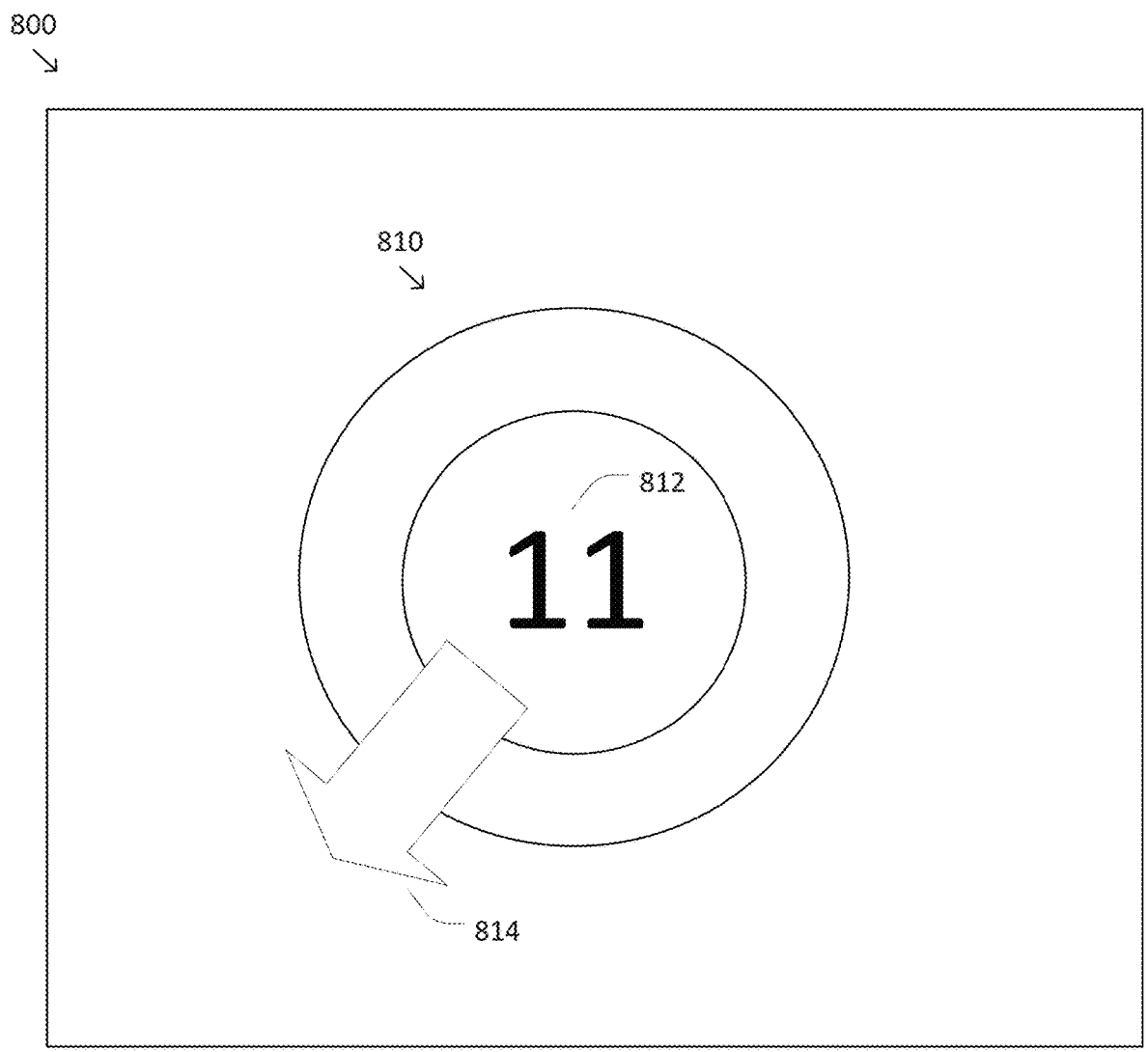
FIG. 8 is a simplified diagram of a window for displaying actuation information.

FIG. 8 illustrates an exemplary window 800 for displaying actuation information according to some embodiments. According to some embodiments consistent with FIGS. 1-4, window 800 may correspond to actuation information window 450. In some examples, window 800 is used to display actuation information associated with a bend radius of a flexible body of the elongate device measured using a shape sensing probe, such as a fiber optic bend sensor, disposed along the length of the elongate device. According to some embodiments, window 800 may display one or more graphical indicators including an actuation information icon 810.

In general, actuation information icon 810 provides actuation information that assists the operator in detecting and/or correcting a problem encountered while controlling the elongate device, such as excessive bending of the elongate device. An excessive bending condition may be problematic, for example, when a medical instrument used during the procedure cannot fit through the elongate device as a result of the excessive bending condition. In some examples, actuation information icon 810 may include an alphanumeric indicator 812 that displays a minimum bend radius of the elongate device to alert the operator to an excessive bending condition. In some examples, the alphanumeric indicator may display a numeric value which continually updates as the tightest bend radius changes but switches to an alpha value (e.g. YES or PASS) when the tightest bend radius equals a value that has been pre-determined to safely allow the passage of an instrument. In some examples, the value may be an alpha value that displays either a PASS or FAIL, YES or NO, and/or another binary indicator of a large enough bend radius down the length of the elongate device to allow for the passage of an instrument.

In some examples, actuation information icon 810 may include a directional indicator 814, such as an arrow, that indicates which direction the operator should steer the elongate device to alleviate the excessive bending condition. In some examples, directional indicator 814 may appear when the excessive bending condition is detected, and may disappear when the excessive bending condition is alleviated. In some examples, the color, size, texture, and/or other attributes of actuation information icon 810, alphanumeric indicator 812, and/or directional indicator 814 may be dynamic so as to convey supplemental guidance information to the operator. For example, different colors may correspond to different ranges of bend radius (e.g., red corresponds to a bend radius of 1-10, green corresponds to a bend radius over 50, and yellow—and/or a gradually shifting shade of color from red to orange to yellow to green—corresponds to a bend radius of 11-49). The color scheme may be applied to actuation information icon 810 and/or portions of thereof, such as the directional indicator 814 and/or the numerical indicator 812.

In the illustrative example depicted in FIG. 8, the minimum bend radius of the elongate device (i.e., the smallest bend radius along the length of the elongate device) is 11 mm, as depicted by alphanumeric indicator 812. The smaller the number, the tighter the bend radius. In order to increase the minimum bend radius, the operator is instructed to navigate a control device, such as a joystick, a trackball, and/or the like, down and to the left, as depicted by the arrow of directional indicator 814. For example, in one or more embodiments, actuation information icon 810 may depict a top view of a trackball used by the operator to control the bend of the elongate device. In furtherance of such embodiments, directional indicator 814 may indicate the direction the trackball should be rolled to straighten the elongate device.

Figure 9:
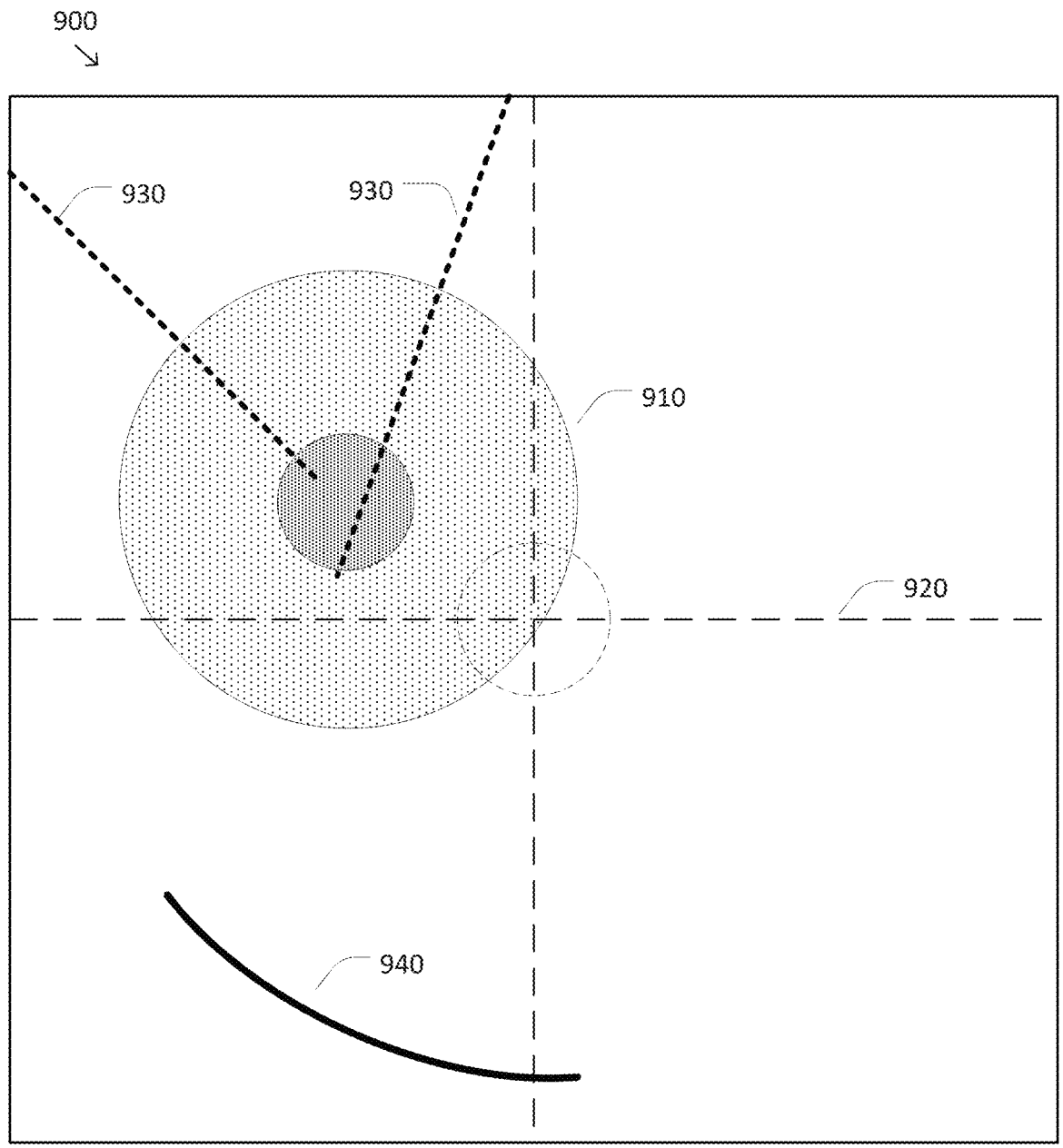
FIG. 9 is a simplified diagram of a window for displaying target guidance information in an alignment mode according to some embodiments.

FIG. 9 illustrates a window 900 for displaying target guidance information in an alignment mode according to some embodiments. According to some embodiments consistent with FIGS. 1-4, window 900 may correspond to target guidance window 460. Window 460 displays a target indicator at target location 910 from a viewpoint corresponding to forward-looking out of a distal end of the elongate device. According to some embodiments, window 900 may display guidance information designed to assist the operator in aligning the elongate device with target location 910 from close range. Unlike a virtual endoscopic view, such as virtual endoscopic view window 420 and/or window 500, window 900 may not depict any anatomical features. The lack of anatomical features in window 900 has the advantage of drawing the attention of the operator to target location 910. The lack of anatomical features in window 900 has the further advantage of reducing the computational complexity involved in rendering window 900, which reduces lag. In some examples, displaying window 900 without any anatomical features is possible in alignment mode because the elongate device has already been navigated to within close range of target location 910 (e.g., within two or three centimeters). For example, there may be no further branches, bends, and/or obstructions in the patient anatomy between the distal end of the elongate device and target location 910. However, in some embodiments, window 900 may include representations of anatomical features, a subset of anatomical features, and/or simplified representations of anatomical features for purposes such as safety, avoidance of anatomical structures (e.g., lesions) close to target location 910, and/or other functional considerations.

In some examples, target location 910 may be represented as a circle and/or a set of concentric circles. In some examples, the shape of target location 910 may be determined using pre-operative medical imaging data. The color, size, texture, shading, and/or transparency of target location 910 may vary depending on the distance between the distal end of the elongate device and target location 910. According to some embodiments, an alignment indicator 920 is displayed in window 900 to identify where a medical instrument is aimed with respect to target location 910. For example, alignment indicator 920 may include crosshairs that mark the center of the window and/or the location within window 900 where a medical procedure (e.g., a biopsy and/or laser ablation) will be performed, which may be off-center and/or in multiple locations. The crosshairs can correspond to a radial center of the elongate which correlates with a centerline axis an instrument delivered through the elongate such as a probe or biopsy needle. According to some embodiments, the color, texture, shading, and/or transparency of alignment indicator 920 may vary based on the quality of the alignment between alignment indicator 920 and target location 910. For example, alignment indicator 920 may turn green when the desired alignment is achieved, yellow when the alignment is close but not fully aligned, and red when misaligned. In some examples, the attribute of target location 910 that changes in response to the distance between the distal end of the elongate device and target location 910 may be different than the attribute of alignment indicator 920 that changes in response to the alignment. In this manner, a confusing situation is avoided in which, for example, the colors of target location 910 and alignment indicator 920 change at the same time in different ways. The quality of the alignment between the alignment indicator 920 and the target location 910 and/or the distance between the distal end of the elongate device and the target location 910 can be determined by a sensed position and/or orientation of the elongate device based on a tracking system, such as tracking system 230. In some examples, window 900 may additionally or alternately display a side view between the distal end of the elongate device and target location 910. The side view may be helpful for visualizing the distance between the distal end of the elongate device and target location 910, as the distance is otherwise orthogonal to the perspective depicted in FIG. 9.

In some examples, one or more indicators 930 may be displayed in window 900 to indicate the location of previous procedures performed at target location 910. For example, when biopsies have previously been collected from various entry angles, the operator may find it useful to visualize the different previous approaches when lining up for a current biopsy. Indicators 930 may be displayed based on stored needle trajectory information. In some examples, needle trajectory information is generated and stored when the operator manually indicates that a biopsy is being taken, at which point the needle trajectory is calculated based on the current position and orientation of the elongate device. In some examples, the onset of a biopsy is automatically detected based on information from a shape sensor at the distal end of the elongate device that generates a signal when the needle exits the distal end of the elongate device. In some examples, the needle may be robotically controlled and/or may include a position sensor, in which case the time and depth of needle insertion can be directly captured and stored. In some examples, fluoroscopic imaging may be used to detect when and where the needle is extended from the elongate device. In some examples, indicators 930 may be numbered, time stamped, and/or supplemented with clinical information pertaining to the previous attempts.

In some examples, a range of motion limit indicator 940 may be displayed in window 900 to indicate that the elongate device cannot or should not be steered any further in a particular direction. In some examples, range of motion limit indicator 940 may appear when a pressure sensor detects excessive pressure on the elongate device from a given direction, as may occur when steering the elongate device into a wall of an anatomical passageway and/or when range of motion limits of a steerable portion of the elongate device are approached and/or exceeded. In some examples, range of motion limits may be determined based on physical constraints, such as an inability of the steering mechanism to bend the elongate device any further, and/or practical constraints, such as a minimum bend radius beyond which a medical instrument cannot be safely inserted through the elongate device. In this manner, range of motion limit indicator 940 alerts the operator to the violation of one or more built-in and/or external limits that prohibits further steering of the elongate device in one or more directions. In response to observing range of motion limit indicator 940, the operator may steer the elongate device in the opposite direction until range of motion limit indicator 940 disappears and/or otherwise changes state to indicate that the condition has been addressed. According to some embodiments, range of motion limit indicator 940 may be displayed as an arc. Various attributes of the arc, such as the radius, angle, length, width, color, texture, shade, transparency, and/or the like may vary to indicate the severity of the limit violation (e.g., yellow to indicate that the range of motion limit is being approached, red to indicate that the limit has been reached and/or exceeded).

Figure 10:
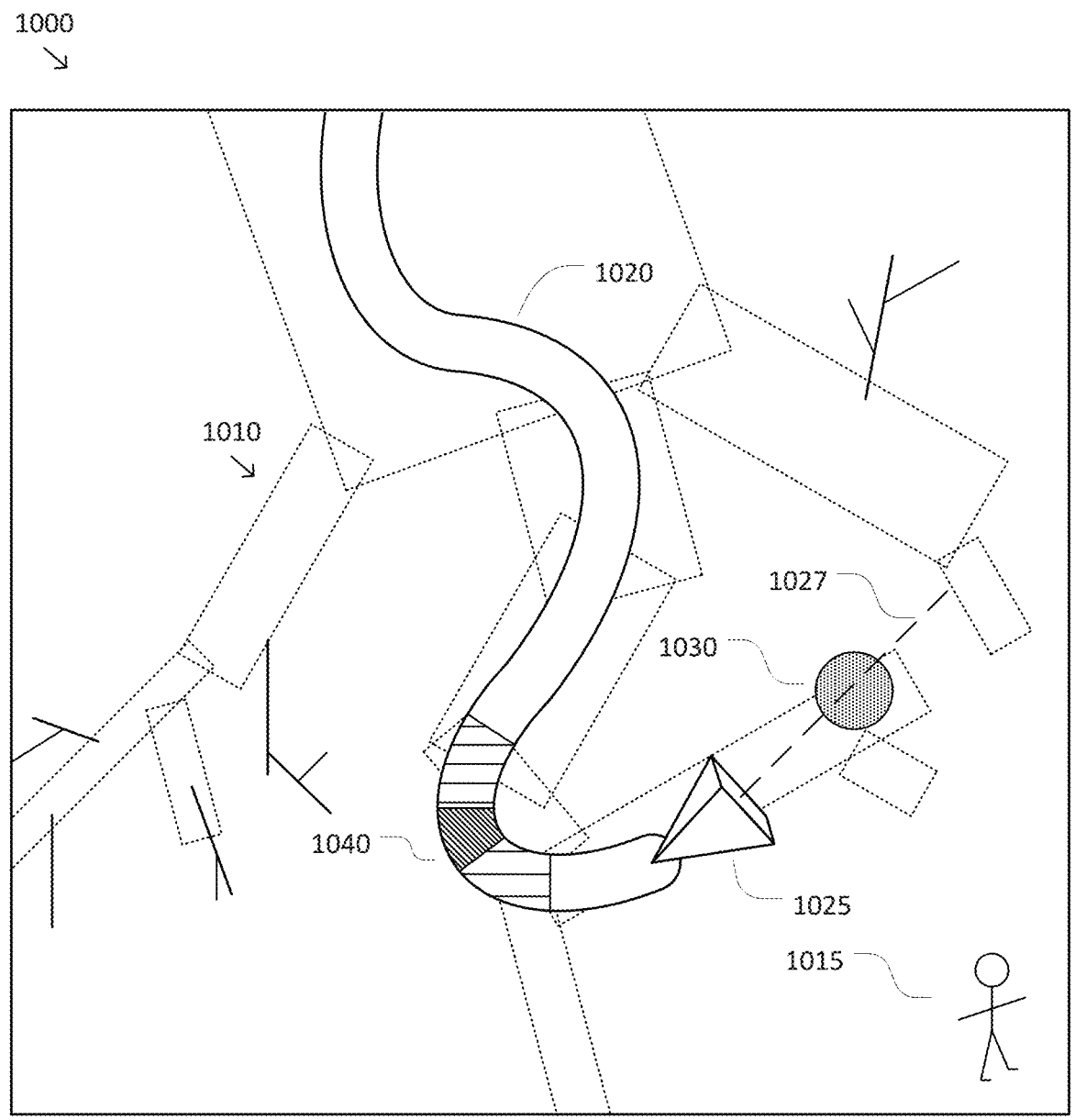
FIG. 10 is a simplified diagram of a window for displaying virtual global images in an alignment mode according to some embodiments.

FIG. 10 illustrates a window 1000 for displaying virtual global images in an alignment mode according to some examples. According to some embodiments consistent with FIGS. 1-4, window 1000 may correspond to virtual global view windows 470-480. Like window 600 depicted in FIG. 6, window 1000 displays anatomical features 1010 and an elongate device 1020 with a field of view indicator 1025 from a global perspective. Likewise, an orientation indicator 1015 and a target location 1030 generally correspond to orientation indicator 615 and target location 1030, respectively. In some examples, a centerline 1027 from the distal end of elongate device 1020 is displayed in order to help the operator visualize the insertion of a medical instrument, such as a biopsy needle, into target location 1030.

In some examples, window 1000 may provide a simplified view of anatomical features 1010 relative to anatomical features 610 of window 600. For example, rather than depict anatomical features with a high degree of detail and/or realism, anatomical features 1010 may use basic two and/or three dimensional shapes (e.g. rectangles, cubes, cylinders, spheres) to depict anatomical passageways. Like the lack of anatomical features in window 900, depicting anatomical features 1010 using basic shapes has the advantage of reducing the computational complexity involved in rendering window 1000, which may reduce lag and thereby improve the ability to make fine alignment adjustments. Additional simplifications, such as the lack of a virtual roadmap (e.g., virtual roadmap 635), are possible and/or desirable in the alignment mode due to the fact that elongate device 1020 is in close range of target location 1030.

In some examples, a medical instrument may be inserted into elongate device 1020 in the alignment mode. Accordingly, it would be desirable to know whether the medical instrument to be inserted is able to safely pass through elongate device 1020. For example, it would be desirable to know whether any portions of elongate device 1020 are excessively bent and/or otherwise compromised (e.g., chemically, thermally, mechanically, and/or biologically compromised). To address this challenge, color scheme 1040 of elongate device 1020 indicates the bend radius (and/or temperature, strain, and/or the like) of elongate device 1020 at different positions along its length. Color scheme 1040 may be used to display the measured bend radius by varying the color, texture, pattern, transparency, shade and/or another visual property of elongate device 1020 as a function of position. Using color scheme 1040, different colors and/or shades may be assigned to ranges of bend radius values (e.g., green may be assigned to a range that is considered straight and red may be assigned to a range that is considered bent, while yellow may be assigned to intermediate ranges). As depicted in FIG. 10, a color scheme is adopted in which darker portions of elongate device 1020 correspond to a smaller bend radius. Such a color scheme may alert the operator to possible portions of elongate device 1020 that are excessively bent. For example, a region of elongate device 1020 may turn red when bent beyond a threshold value. According to some embodiments, the threshold value may correspond to a bend radius at which a device, such as a needle, can no longer freely pass through elongate device 1020. In some examples, the threshold value may correspond to a minimum bend radius of elongate device 1020, such as a radius at which elongate device 1020 becomes susceptible to forming kinks. In some embodiments, there may be multiple threshold values, with each threshold value triggering a different change in color scheme 1040, such as a transition to a darker hue of red to indicate that a more extreme threshold has been exceeded. Although transitions between colors are depicted as being abrupt, it is to be understood that color scheme 1040 may gradually transition between colors in some examples so that a property of color scheme 1040, such as hue, brightness, and/or the like, is computed as a function of the bend radius. In some examples, color scheme 1040 may be applied along the entire length of elongate device 1020. In some examples, color scheme 1040 may be limited to a distal portion of elongate device 1020, as a proximal portion of elongate device 1020 may not be as susceptible as the distal portion to becoming excessively bent.

In general, any one of windows 500-900 may include features from any other windows as appropriate. For example, window 500 may include an orientation indicator, such as orientation indicator 615 of window 600. In some examples, elongate device 620 may include a color scheme, such as color scheme 1040 of elongate device 1020. In some examples, window 1000 may include a virtual roadmap, such as virtual roadmap 635 of window 600. In some examples, window 1000 may include indicators of the location of previous procedures performed at target location 1030, such as indicators 930 of window 900. In some examples, detailed anatomical features 610 of window 600 may be simplified to resemble anatomical features 1010, in order to improve rendering efficiency. Conversely, simplified anatomical features 1010 of window 1000 may be enhanced to resemble anatomical features 610, in order to improve the aesthetics of window 1000.

In some examples, it may be desirable to measure the position and/or shape of an elongate device using a shape sensor when the elongate device is "parked" (i.e., when the operator is not inserting, retracting, and/or articulating the elongate device). For example, the elongate device may be displaced when a medical instrument, such as a needle, is inserted into and/or removed from the elongate device. To depict this movement in multi-modal graphical user interface 400, the original position of the elongate device (prior to being displaced) may be depicted as a transparent and/or semi-transparent "ghost" view in one or more of virtual global view windows 430, 470, and/or 480. In some examples, it may be desirable to alert the operator when the patient body moves. For example, patient movement may be detected using a sensor in a patient pad and/or the like. When patient movement is detected, one or more attributes of multi-modal graphical user interface 400 may change, such as a background and/or border color changing to red. In some example, image data, such as the representation of anatomical features 610 and/or 1010, may change color, shade, texture, and/or transparency. In some examples, these changes may be triggered when patient movement exceeds one or more predetermined thresholds.

Figure 11:
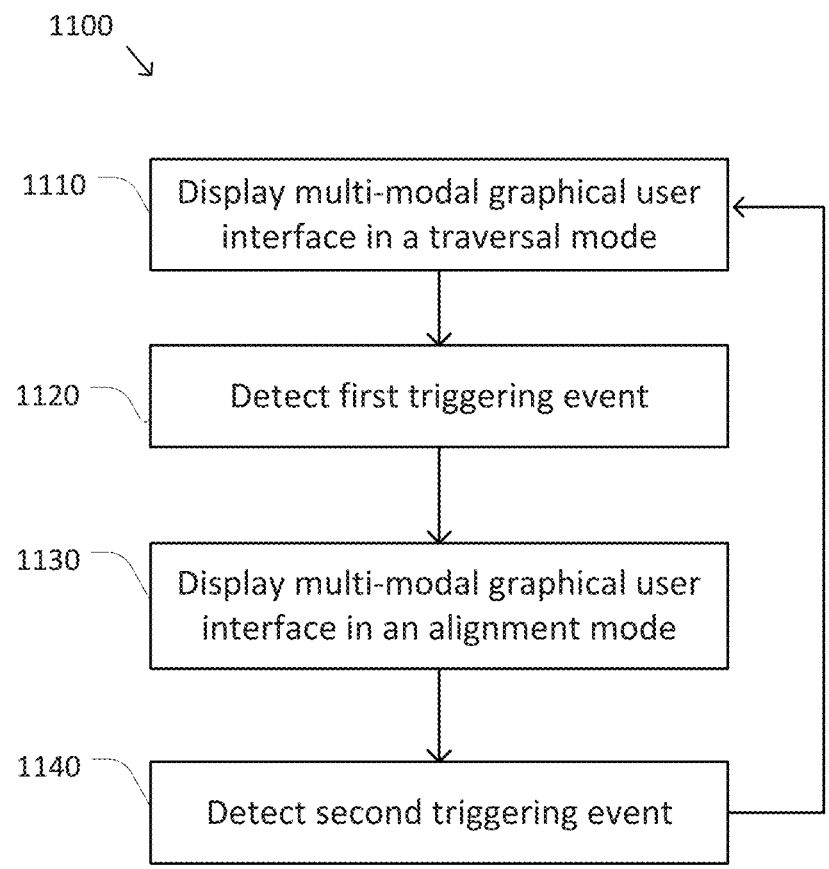
FIG. 11 is a simplified diagram of a method of displaying a multi-modal graphical user interface during an image-guided surgical procedure according to some embodiments.

FIG. 11 is a flowchart illustrating a method 1100 of displaying a multi-modal graphical user interface, such as multi-modal graphical user interface 400, during an image-guided surgical procedures according to some embodiments. Method 1100 is illustrated as a set of operations or processes 1110-1140. Not all of the illustrated processes 1110-1140 may be performed in all embodiments of method 1100. Additionally, one or more processes that are not expressly illustrated in FIG. 11 may be included before, after, in between, or as part of the processes 1110-1040. In some embodiments, one or more of the processes 1110-1140 of method 1100 may be implemented, at least in part, in the form of executable code stored on non-transitory, tangible, computer readable media that when run by one or more processors (e.g., the processors of control system 112) may cause the one or more processors to perform one or more of the processes 1110-1140.

At a process 1110, the multi-modal graphical user interface is displayed in a traversal mode. In some embodiments consistent with FIGS. 1-10, the traversal mode may include a live camera view window, a virtual endoscope view window, a virtual global view window, a settings window, and/or an actuation information window. In some embodiments, the traversal mode is used when driving an elongate device through a patient body, wherein substantial movement associated with insertion, retraction, and/or articulation of the elongate device is expected. In some examples, a camera probe is inserted into the elongate device and positioned at the distal end of the elongate device in traversal mode to provide live image data.

At a process 1120, a first triggering event is detected indicating that the multi-modal graphical user interface is to transition from the traversal mode to the alignment mode. The first triggering event may include a user initiated trigger and/or an automatically detected triggering condition. A manual trigger may include a physical input from the operator by, for example, clicking a button, flipping a switch, using a touchpad, and/or any other suitable manual input. In some examples, an automatically detected triggering condition may include removing a camera probe from the elongate device. In some examples, the removal of the camera probe from the elongate device may be detected based on a change in shape of the elongate device, as determined using a shape sensor such as shape sensor 222. In some examples, the removal of the camera probe from the elongate device may be detected based on a change in the image data provided by the camera probe, as determined using an image processor. In some examples, the change in image data may be provided from a real imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The change in image data can include a new image being acquired using the imaging technology at a different angle relative to a target or at a different time in the procedure. The triggering condition may include the attachment or disconnection of the imaging technology from the system. In some examples, a triggering condition may include inserting a medical instrument into the elongate device. Like the removal of the camera probe from the elongate device, the insertion of the medical instrument into the elongate device may be determined based on a change in shape of the c elongate device. In some examples, the triggering condition may include detecting that the distal end of the elongate device is within a predetermined distance (e.g., two or three centimeters) of a target location. In some examples, the triggering condition may include determining that there is a line of sight between the distal end of the elongate device and the target location (i.e., no obstructions and/or bends in anatomical passageways). In some examples, the triggering condition may include detecting that there are no remaining branches in the anatomical passageways separating the distal end of the elongate device and the target location, meaning that there is no remaining risk of getting "lost" by navigating down the wrong branch. In some examples, the triggering condition may include reaching the end of a predetermined route to the target location. In some examples, the triggering condition may include detecting that the operator has stopped inserting the elongate device (i.e., when the elongate device has been "parked"). In some examples, the triggering condition may include a change in In some examples, the operator may have the option of overriding the automatic trigger by providing a manual trigger. In some examples, any suitable combination of one or more triggering conditions may be used to automatically switch between the traversal and alignment modes. For example, a triggering condition may include detecting that both of the following conditions are concurrently satisfied: (1) the elongate device is within a predetermined distance of the target location and (2) the operator has stopped inserting the elongate device. When the first triggering event is detected, method 1100 may proceed to process 1130 for displaying the multi-modal graphical user interface in an alignment mode.

At a process 1130, the multi-modal graphical user interface is displayed in an alignment mode. In some embodiments consistent with FIGS. 1-10, the alignment mode may include a target guidance window, one or more virtual global view windows, a settings window, and/or an actuation information window. In some embodiments, the alignment mode is used when optimizing the position and/or orientation of the elongate device in relation to a target location in preparation for performing a medical procedure (e.g., a biopsy, laser ablation, imaging, and/or the like). In some examples, there is no camera probe is inserted in the elongate device in alignment mode, so the elongate device is being steered "blindly."

At a process 1140, a second triggering event is detected indicating that the multi-modal graphical user interface is to transition from the alignment mode to the traversal mode. In some examples, the second triggering events may be substantially similar to the first triggering events but in reverse order. For example, rather than detecting the removal of a camera probe from the elongate device, the reinsertion of the camera probe into the elongate device may serve as an example of a second triggering event. When the second triggering event is detected, method 1100 may proceed to process 1110 for displaying the multi-modal graphical user interface in the traversal mode.

Figure 12:
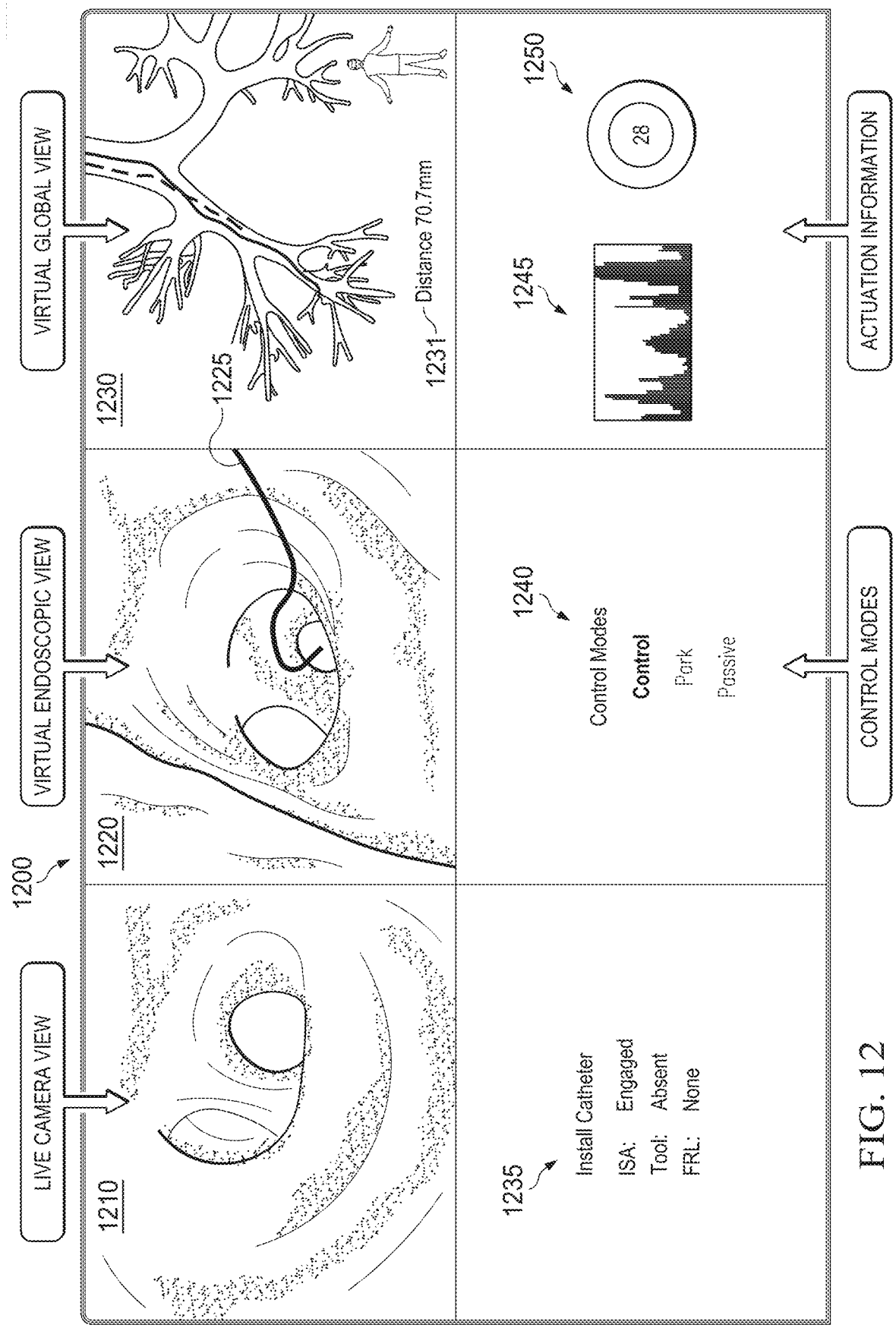
FIG. 12 is a screenshot of a multi-modal graphical user interface in a traversal mode.

FIG. 12 is a screenshot 1200 of a multi-modal graphical user interface, such as multi-modal graphical user interface 400, in a traversal mode according to some embodiments. Like multi-modal graphical user interface 400 in the traversal mode, screenshot 1200 depicts five concurrently viewable frames or windows 1210-1250. Windows 1210-1250 generally correspond to windows 410-450, as depicted in FIG. 4a. In some examples, window 1220 for displaying a virtual endoscopic view includes a virtual roadmap 1225 as a green line leading to a target location. In some examples, window 1230 for displaying a virtual global view includes a distance indicator 1231 to indicate the distance between a distal end of the elongate device and the target location.

FIG. 13 is a screenshot 1300 of a multi-modal graphical user interface, such as multi-modal graphical user interface 400, in an alignment mode according to some embodiments. Like multi-modal graphical user interface 400 in the alignment mode, screenshot 1300 depicts six concurrently viewable frames or windows 1310 and 1340-1380. Windows 1310 and 1340-1380 generally correspond to windows 410 and 440-480 as depicted in FIG. 4*b*.

Some examples of control units, such as control unit 130 may include non-transient, tangible, machine readable media that include executable code that when run by one or more processors (e.g., processor 140) may cause the one or more processors to provide graphical user interface 400 or perform the processes of method 1100. Some common forms of machine readable media that may provide graphical user interface 400 or include the processes of method 1100 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Additional Examples

A1. A method for displaying guidance information using a graphical user interface during a medical procedure, the method comprising: displaying first image data from a perspective corresponding to a distal end of an elongate device, wherein the first image data includes anatomical features of a patient anatomy; displaying a virtual roadmap to a target location within the patient anatomy, wherein the virtual roadmap indicates a predetermined route to the target location; and changing one or more of color, shade, texture, and transparency of the virtual roadmap based on a deviation between a distal end of the elongate device and the predetermined route.

A2. The method of example A1, wherein the virtual roadmap is displayed as a line superimposed on the anatomical features included in the first image data.

A3. The method of example A1 or A2, wherein the virtual roadmap changes one or more of color, shade, texture, and transparency based on one or more attributes of the anatomical features, the one or more attributes being selected from a group consisting of a diameter of an anatomical passageway, a bend of the anatomical passageway, a constriction of the anatomical passageway, and a branching of the anatomical passageway.

A4. The method of any one of examples A1-A3, wherein the virtual roadmap changes one or more of color, shade, texture, and transparency based on a distance between the distal end of the elongate device and the target location.

A5. The method of any one of examples A1-A4, wherein displaying the first image data further includes displaying a roadblock indicator.

A6. The method of example A5, wherein the anatomical features include an undesirable anatomical feature in which the elongate device should not be directed and the roadblock indicator corresponds to the undesirable anatomical feature.

A7. The method of example A5 or A6, wherein the roadblock indicator is determined based on one or more attributes of the anatomic features, the one or more attributes including diameter of the anatomical feature or bend of the anatomical feature.

A8. The method of any one of examples A1-A7, wherein the anatomical features change one or more of color, shade, texture, and transparency based on a distance between the distal end of the elongate device and the target location.

A9. The method of any one of examples A1-A8, further comprising displaying second image data from a perspective corresponding to the distal end of the elongate device, wherein: the second image data includes a target indicator corresponding to the target location and an alignment indicator corresponding to an expected location of the medical procedure; and the target indicator changes one or more of color, shade, texture, and transparency based on an alignment between the expected location of the medical procedure and the target location.

A10. The method of example A9, wherein the target indicator is modeled based on preoperative voxel data.

A11. The method of example A9 or A10, wherein the target indicator changes one or more of color, shade, texture, and transparency based on a distance between the distal end of the elongate device and the target location.

A12. The method of any one of examples A9-A11, wherein the target indicator changes one or more of color, shade, texture, and transparency based on a deviation between the alignment indicator and the target indicator.

A13. The method of any one of examples A9-A12, wherein the alignment indicator changes one or more of color, shade, texture, and transparency based on a deviation between the alignment indicator and the target indicator.

A14. A method for displaying guidance information using a graphical user interface during a medical procedure, the method comprising: displaying, in an alignment mode of the graphical user interface and during alignment of a distal end of an elongate device to perform the medical procedure at a target location, first image data from a perspective corresponding to the distal end of the elongate device, wherein the first image data includes a target indicator corresponding to the target location and an alignment indicator corresponding to an expected location of the medical procedure; delivering an instrument to the target location, wherein delivering the instrument into the target location includes storing a plurality of instrument trajectories; and displaying a plurality of historical indicators corresponding to the plurality of instrument trajectories.

A15. The method of example A14, wherein the instrument is a needle.

A16. The method of example A14 or A15, further comprising: displaying, in a traversal mode of the graphical user interface and during traversal of an elongate device through an anatomical passageway, second image data from a perspective corresponding to the distal end of the elongate device, wherein the second image data includes a virtual roadmap and a historical path of the elongate device.

A17. The method of example A16, further comprising hiding the historical path based on a manual input.

A18. The method of any one of examples A14-A17, further comprising hiding the historical indicators based on a manual input.

A19. The method of any one of examples A14-A18, wherein the medical procedure is one or more of a biopsy and an ablation.

A20. The method of any one of examples A14-A19, further comprising displaying a force indicator, wherein the force indicator includes a representation of insertion force exerted by motors or actuators used to advance the elongate device.

A21. The method of example A20, wherein the force indicator is displayed as a scrolling bar graph.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method for displaying guidance information using a graphical user interface during a medical procedure, the method comprising:
    displaying, in a first mode of the graphical user interface, first image data as viewed from a distal end of an elongate device, wherein the first image data includes a virtual roadmap;
    transitioning from the first mode of the graphical user interface to a second mode of the graphical user interface wherein the transition is based on an occurrence of a triggering condition, wherein the triggering condition includes detection of a change in presence of a medical instrument in the elongate device based on a change in shape of the elongate device, the change in shape being determined using a shape sensor disposed along a length of the elongate device; and
    displaying, in the second mode of the graphical user interface, second image data as viewed from the distal end of the elongate device, wherein the second image data includes a target indicator corresponding to a target location and an alignment indicator corresponding to an expected location of the medical procedure at the target location.

2. The method of claim 1, further comprising determining a position of the distal end of the elongate device, wherein the triggering condition further includes detecting that the distal end of the elongate device is within a predetermined distance of the target location.

3. The method of claim 1, wherein at least one of the first image data or the second image data comprises a live camera view.

4. The method of claim 1, wherein at least one of the first image data or the second image data comprises a virtual image of anatomic passageways.

5. A system for displaying guidance information using a graphical user interface, the system comprising:
    a medical instrument comprising an imaging probe;
    an elongate device including a flexible body and a distal end; and
    one or more processors configured to:
        display, in a first mode of the graphical user interface, first image data as viewed from a distal end of the elongate device, wherein the first image data includes a virtual roadmap;
        transition from the first mode of the graphical user interface to a second mode of the graphical user interface, wherein the transition is based on an occurrence of a triggering condition that includes a change in presence of the medical instrument within the elongate device, the change in presence of the imaging probe being detected based on a change in video data provided by the imaging probe, the change in the video data being determined using an image processor; and
        display, in the second mode of the graphical user interface, second image data as viewed from the distal end of the elongate device, wherein the second image data includes a target indicator corresponding to a target location and an alignment indicator corresponding to an expected location of a medical procedure at the target location;
    wherein removal of the imaging probe from the elongate device places the graphical user interface in the second mode or placement of the imaging probe within the elongate device places the graphical user interface in the first mode.

6. The system of claim 5, wherein the first mode of the graphical user interface is displayed during traversal of the elongate device through an anatomical passageway and wherein the second mode of the graphical user interface is displayed during alignment of a distal end of the elongate device to perform the medical procedure at the target location.

7. The system of claim 5, wherein the target indicator changes one or more of color, shade, texture, or transparency based on at least one of a distance between the distal end of the elongate device and the target location or based on a deviation between the alignment indicator and the target indicator.

8. The system of claim 5, wherein the alignment indicator changes one or more of color, shade, texture, or transparency based on a deviation between the alignment indicator and the target indicator.

9. The system of claim 5, wherein the change in presence of the medical instrument is further detected based on a change in shape of the elongate device, the change in shape being determined using a shape sensor disposed along a length of the elongate device.

10. The system of claim 9, further comprising a biopsy needle, wherein removal of the biopsy needle from the elongate device places the graphical user interface in the first mode or placement of the biopsy needle within the elongate device places the graphical user interface in the second mode.

11. The system of claim 5, wherein the one or more processors are further configured to determine a position of the distal end of the elongate device and the triggering condition further includes detecting that the distal end of the elongate device is within a predetermined distance of the target location.

12. The system of claim 11, further comprising a sensor disposed along a length of the elongate device that determines the position of the distal end of the elongate device, wherein the sensor comprises at least one of an electromagnetic sensor or a fiber optic shape sensor.

13. The system of claim 5, wherein:
    the first image data further includes anatomical features of a patient anatomy;
    the virtual roadmap indicates a predetermined route to the target location; and
    the one or more processors are further configured to change one or more of color, shade, texture, or transparency of the virtual roadmap based on a deviation between the distal end of the elongate device and the predetermined route.

14. The system of claim 13, wherein the anatomical features change one or more of color, shade, texture, or transparency based on a distance between a distal end of the elongate device and the target location.

15. The system of claim 13, wherein the virtual roadmap is displayed as a line superimposed on the anatomical features included in the first image data.

16. The system of claim 13, wherein the virtual roadmap changes one or more of color, shade, texture, or transparency based on one or more attributes of the anatomical features, the one or more attributes including at least one of a diameter of an anatomical passageway, a bend of the anatomical passageway, a constriction of the anatomical passageway, or a branching of the anatomical passageway.

17. The system of claim 13, wherein the virtual roadmap changes one or more of color, shade, texture, or transparency based on a distance between the distal end of the elongate device and the target location.

18. The system of claim 13, wherein displaying the first image data further includes displaying a roadblock indicator.

19. The system of claim 18, wherein the roadblock indicator is determined based on one or more attributes of the anatomic features, the one or more attributes including a diameter of an anatomical passageway or a bend of the anatomical passageway.

20. A non-transitory machine-readable medium comprising a plurality of machine-readable instructions which when executed by one or more processors associated with a guidance display system are adapted to cause the one or more processors to perform a method comprising:

displaying, in a first mode of the guidance display system, first image data as viewed from a distal end of an elongate device, wherein the first image data includes a virtual roadmap;

transitioning from the first mode of the guidance display system to a second mode of the guidance display system wherein the transition is based on an occurrence of a triggering condition, wherein the triggering condition includes a change in presence of a medical instrument in the elongate device based on a change in shape of the elongate device, the change in shape being determined using a shape sensor disposed along a length of the elongate device; and displaying, in the second mode of the guidance display system, second image data as viewed from the distal end of the elongate device, wherein the second image data includes a target indicator corresponding to a target location and an alignment indicator corresponding to an expected location of a medical procedure at the target location.

21. The non-transitory machine-readable medium of claim 20, wherein the virtual roadmap comprises one or more arrows indicating a direction to steer the elongate device.

22. The non-transitory machine-readable medium of claim 20, wherein the virtual roadmap comprises one or more alphanumeric indicators corresponding to at least one of a distance to the target location, a remaining time to reach the target location, or an identity of an anatomical passageway of a set of anatomical passageways.

* * * * *